United States Patent
Yang et al.

(10) Patent No.: US 11,248,258 B2
(45) Date of Patent: Feb. 15, 2022

(54) METHOD FOR CHARACTERIZING BIOLOGICAL PART BASED ON DUAL-FLUORESCENT REPORTER GENE SYSTEM AND BIOLOGICAL PART LIBRARY CONSTRUCTED THEREON

(71) Applicant: HUBEI UNIVERSITY, Hubei (CN)

(72) Inventors: Shihui Yang, Hubei (CN); Yongfu Yang, Hubei (CN); Wei Shen, Hubei (CN); Runxia Li, Hubei (CN); Ju Huang, Hubei (CN); Yu Wang, Hubei (CN); Li Yi, Hubei (CN); Lixin Ma, Hubei (CN)

(73) Assignee: Hubei University, Hubei (CN)

( * ) Notice: Subject to any disclaimer, the term of this patent is extended or adjusted under 35 U.S.C. 154(b) by 97 days.

(21) Appl. No.: 16/769,558

(22) PCT Filed: May 9, 2019

(86) PCT No.: PCT/CN2019/086173
§ 371 (c)(1),
(2) Date: Jun. 3, 2020

(87) PCT Pub. No.: WO2020/164195
PCT Pub. Date: Aug. 20, 2020

(65) Prior Publication Data
US 2020/0385795 A1    Dec. 10, 2020

(30) Foreign Application Priority Data

Feb. 14, 2019  (CN) .......................... 201910114635.7
Feb. 14, 2019  (CN) .......................... 201910114652.0
Feb. 14, 2019  (CN) .......................... 201910114932.1

(51) Int. Cl.
*C12Q 1/6851* (2018.01)
*C12N 15/74* (2006.01)
*C12Q 1/6806* (2018.01)
*C40B 40/02* (2006.01)

(52) U.S. Cl.
CPC .......... *C12Q 1/6851* (2013.01); *C12N 15/74* (2013.01); *C12Q 1/6806* (2013.01); *C40B 40/02* (2013.01)

(58) Field of Classification Search
None
See application file for complete search history.

(56) References Cited

FOREIGN PATENT DOCUMENTS

| CN | 103382505 A | 11/2013 |
| CN | 105555947 A | 5/2016 |
| CN | 108018301 A | 5/2018 |

OTHER PUBLICATIONS

Yang et al. Prediction and characterization of promoters and ribosomal binding sites of Zymomonas mobilis in system biology era. Published online Mar. 14, 2019. Biotechnology for Biofuels. vol. 12, No. 52, p. 1-13. (Year: 2019).*

Geng et al., Application research progress of dual-luciferase reporter gene system, Science & Technology Information, 2012, No. 21, p. 1.

* cited by examiner

*Primary Examiner* — Channing S Mahatan

(57) ABSTRACT

A method for identifying and characterizing biological parts based on omics datasets and a dual-fluorescent reporter gene system, and a biological part library constructed thereon are provided, relating to a technical filed of biology. The method includes steps of: identifying the biological parts using the omics datasets; constructing a single-fluorescent reporter gene system using a shuttle vector pEZ15Asp as a skeleton for screening and determining fluorescent reporter genes; obtaining a dual-fluorescent reporter gene system skeleton; constructing recombinant plasmids, and finally transforming into competent cells for quantitative analysis of fluorescence intensities. The present invention is convenient and quick, and can screen and identify different biological parts such as RBS, UTRs, promoters, and terminators of different intensities in batch quantitatively in a relatively short time. Moreover, the present invention can quickly expand the biological part library of *Z. mobilis*, so as to be applied in metabolic engineering of different demands.

18 Claims, 7 Drawing Sheets
Specification includes a Sequence Listing.

**Verification of P*tet* inducible dual-fluorescent reporter gene system with qPCR**

**Verification of P*tet* inducible dual-fluorescent reporter gene system with FCM**

FCM modes of promoters of different intensities

SEQUENCE LISTING

<160> NUMBER OF SEQ ID NOS: 74

<210> SEQ ID NO 1
<211> LENGTH: 33
<212> TYPE: DNA
<213> ORGANISM: Artificial Sequence
<220> FEATURE:
<223> OTHER INFORMATION: The sequence is synthetized.

<400> SEQUENCE: 1
gcgctagcgg agtgtatact ggcttactat gtt                                 33

<210> SEQ ID NO 2
<211> LENGTH: 26
<212> TYPE: DNA
<213> ORGANISM: Artificial Sequence
<220> FEATURE:
<223> OTHER INFORMATION: The sequence is synthetized.

<400> SEQUENCE: 2
acggtgagct ggtgacctgc cttatc                                         26

<210> SEQ ID NO 3
<211> LENGTH: 18
<212> TYPE: DNA
<213> ORGANISM: Artificial Sequence
<220> FEATURE:
<223> OTHER INFORMATION: The sequence is synthetized.

<400> SEQUENCE: 3
atggtgagca agggcgag                                                  18

<210> SEQ ID NO 4
<211> LENGTH: 17

```
<212> TYPE: DNA
<213> ORGANISM: Artificial Sequence
<220> FEATURE:
<223> OTHER INFORMATION: The sequence is synthetized.

<400> SEQUENCE: 4
actagtagcg gccgctg                                                  17

<210> SEQ ID NO 5
<211> LENGTH: 305
<212> TYPE: DNA
<213> ORGANISM: Zymomonas mobilis

<400> SEQUENCE: 5
gttcgatcaa caacccgaat cctatcgtaa tgatgttttg cccgatcagc ctcaatcgac    60
aattttacgc gtttcgatcg aagcagggac gacaattggc tgggaacggt atactggaat  120
aaatggtctt cgttatggta ttgatgtttt tggtgcatcg gccccggcga atgatctata  180
tgctcatttc ggcttgaccg cagtcggcat cacgaacaag gtgttggccg cgatcgccgg  240
taagtcggca cgttaaaaaa tagctatgga atatagtagc tacttaataa gttaggagaa  300
taaac                                                             305

<210> SEQ ID NO 6
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 6
gcggccgcta ctagtgttcg atcaacaacc cgaatc                             36

<210> SEQ ID NO 7
<211> LENGTH: 42
<212> TYPE: DNA
<213> ORGANISM: Artificial Sequence
<220> FEATURE:
<223> OTHER INFORMATION: The sequence is synthetized.

<400> SEQUENCE: 7
gcccttgctc accatgttta ttctcctaac ttattaagta gc                      42

<210> SEQ ID NO 8
<211> LENGTH: 25
<212> TYPE: DNA
<213> ORGANISM: Artificial Sequence
<220> FEATURE:
<223> OTHER INFORMATION: The sequence is synthetized.

<400> SEQUENCE: 8
ccgctcacaa ttccacacat tatac                                         25

<210> SEQ ID NO 9
<211> LENGTH: 17
<212> TYPE: DNA
<213> ORGANISM: Artificial Sequence
<220> FEATURE:
<223> OTHER INFORMATION: The sequence is synthetized.

<400> SEQUENCE: 9
accaggatgg gcaccac                                                  17

<210> SEQ ID NO 10
```

<211> LENGTH: 1495
<212> TYPE: DNA
<213> ORGANISM: Zymomonas mobilis

<400> SEQUENCE: 10

```
aacttgagag tttgattctg gctcagaacg aacgctggcg gcatgcttaa cacatgcaag      60
tcgaacgaag gcttcggcct tagtggcgca cgggtgcgta acgcgtggga atctgccttc     120
aggtacggaa taactagggg aaactcgagc taataccgta tgacatcgag agatcaaaga     180
tttatcgcct gaagatgagc ccgcgttgga ttagctagtt ggtagggtaa aagcttacca     240
aggcgacgat ccatagctgg tctgagagga tgatcagcca cactgggact gagacacggc     300
ccagactcct acgggaggca gcagtgggga atattggaca tgggggaaa ccctgatcca      360
gcaatgccgc gtgagtgaag aaggccttag ggttgtaaag ctcttttacc cgggatgata     420
atgacagtac cggagaata gctccggct aactccgtgc cagcagccgc ggtaatacgg       480
agggagctag cgttgttcgg aattactggg cgtaaagcgt acgtaggcgg tttaataagt     540
cagggggtgaa agcccagagc tcaactctgg aactgccttt gagactgtta gactagaaca   600
tagaagaggt aagtggaatt ccgagtgtag aggtgaaatt cgtagatatt cggaagaaca    660
ccagtggcga aggcgactta ctggtctata gttgacgctg aggtacgaaa gcgtgggtag    720
caaacaggat tagataccct ggtagtccac gccgtaaacg atgataacta gctgtccggg    780
tacatggtat ctgggtggcg gagctaacgc attaagttat ccgcctgggg agtacggtcg    840
caagattaaa actcaaagaa attgacgggg gcctgcacaa gcggtggagc atgtggttta   900
attcgaagca acgcgcagaa ccttaccagc gtttgacatc ctgatcgcgg aaagtggaga    960
cacattcttt cagttcggct ggatcagaga caggtgctgc atggctgtcg tcagctcgtg   1020
tcgtgagatg ttgggttaag tcccgcaacg agcgcaaccc tcacctctag ttgccatcat   1080
taagttgggc actttagagg aactgccggt gataagccgg aggaaggtgg ggatgacgtc   1140
aagtcctcat ggcccttacg cgctgggcta cacacgtgct acaatggcgg tgacagaggg   1200
ccgcaagcct gcaaaggtta gctaatctca aaaagccgtc tcagttcgga ttgttctctg   1260
caactcgaga gcatgaaggc ggaatcgcta gtaatcgcgg atcagcatgc cgcggtgaat   1320
acgttcccag gccttgtaca caccgcccgt cacaccatgg gagttggatt cacccgaagg   1380
cgctgcgcta acccgcaagg gaggcaggcg accacggtgg gtttagcgac tggggtgaag   1440
tcgtaacaag gtagccgtag gggaacctgc ggctggatca cctcctttct aagga         1495
```

<210> SEQ ID NO 11
<211> LENGTH: 24
<212> TYPE: DNA
<213> ORGANISM: Zymomonas mobilis

<400> SEQUENCE: 11

```
ccataatcta gagaaagtaa gcac                                              24
```

<210> SEQ ID NO 12
<211> LENGTH: 27
<212> TYPE: DNA
<213> ORGANISM: Zymomonas mobilis

<400> SEQUENCE: 12

```
aggctaagaa ctaacggaga ggtaaat                                           27
```

<210> SEQ ID NO 13
<211> LENGTH: 26

```
<212> TYPE: DNA
<213> ORGANISM: Zymomonas mobilis

<400> SEQUENCE: 13
atcacagggt ctagaaggag gtcgaa                                              26

<210> SEQ ID NO 14
<211> LENGTH: 20
<212> TYPE: DNA
<213> ORGANISM: Zymomonas mobilis

<400> SEQUENCE: 14
gagcgagaag gaggtaaagt                                                     20

<210> SEQ ID NO 15
<211> LENGTH: 48
<212> TYPE: DNA
<213> ORGANISM: Artificial Sequence
<220> FEATURE:
<223> OTHER INFORMATION: The sequence is synthetized.

<400> SEQUENCE: 15
gcggccgcta ctagtttaag acccactttc acatttaagt tgtttttc                      48

<210> SEQ ID NO 16
<211> LENGTH: 80
<212> TYPE: DNA
<213> ORGANISM: Artificial Sequence
<220> FEATURE:
<223> OTHER INFORMATION: The sequence is synthetized.

<400> SEQUENCE: 16
gcccttgctc accatgtgct tactttctct agattatgga gatcatttga atacttttct         60
ctatcactga tagggagtgg                                                     80

<210> SEQ ID NO 17
<211> LENGTH: 305
<212> TYPE: DNA
<213> ORGANISM: Zymomonas mobilis

<400> SEQUENCE: 17
gttcgatcaa caacccgaat cctatcgtaa tgatgttttg cccgatcagc ctcaatcgac         60
aattttacgc gtttcgatcg aagcagggac gacaattggc tgggaacggt atactggaat       120
aaatggtctt cgttatggta ttgatgtttt tggtgcatcg gccccggcga atgatctata       180
tgctcatttc ggcttgaccg cagtcggcat cacgaacaag gtgttggccg cgatcgccgg       240
taagtcggca cgttaaaaaa tagctatgga atatagtagc tacttaataa gttaggagaa       300
taaac                                                                    305

<210> SEQ ID NO 18
<211> LENGTH: 947
<212> TYPE: DNA
<213> ORGANISM: Zymomonas mobilis

<400> SEQUENCE: 18
aaagtcacac ggttccttat ttctttttcta tccaaactct ttgcaatagt ctgtaacaag        60
atgacggcga cgatatcgga tcttcgtctc ttttgggtcg cgaaaaaata ttaactttaa       120
tcgaaaaaaa ttgagtctgt ttttactcgg gacaagaccg cctttttttta tccaaagaat      180 atcccttcca tcttctttcg aaagcgaaaa ataaatactg aaaacaacgg ttttgaccac       240
```

```
aagattcacg ggctatcctt caaaagaaga agccctttt tatcctctct tagggcgtgg      300
ttaagggttg gcttgggctt aacaaatttt gtttatgcac aactttgggt tgacttggcg      360
acaataaaat atcaccagag gggcagaccg gttacggaaa cgtttccgct ttgatagctc      420
agacggaggg aaaggctttg tcagtgttgc ggtataatat ctgtaacagc tcattgataa      480
agccggtcgc tcgcctcggg cagttttgga ttgatcctgc cctgtcttgt ttggaattga      540
tgaggccgtt catgcaaaca gccggaaaaa ttttaaaaca ggcgtcttcg gctgctttag      600
gtctcggcta cgtttctaca tctggttctg attcccggtt tacctttttc aaggtgtccc      660
gttccttttt cccctttttg gaggttggtt atgtcctata atcacttaat ccagaaacgg      720
gcgtttagct ttgtccatca tggttgttta tcgctcatga tcgcggcatg ttctgatatt      780
tttcctctaa aaaagataaa aagtcttttc gcttcggcag aagaggttca tcatgaacaa      840
aaattcggca ttttaaaaaa tgcctatagc taaatccgga acgacacttt agaggtttct      900
gggtcatcct gattcagaca tagtgttttg aatatatgga gtaagca                   947
```

```
<210> SEQ ID NO 19
<211> LENGTH: 103
<212> TYPE: DNA
<213> ORGANISM: Zymomonas mobilis

<400> SEQUENCE: 19
ttaaatactg gcataaaccg aaaaatgtcg ttatgagcgc gccggagaag cgcggcgcgc      60
tcaatacaat agtgataaaa gcggtaacaa aaagaggtaa cta                       103
```

```
<210> SEQ ID NO 20
<211> LENGTH: 201
<212> TYPE: DNA
<213> ORGANISM: Zymomonas mobilis

<400> SEQUENCE: 20
tgtctatact ccagttactc aatacgtaac aataatcagt ttatcctaac tatagaatcg      60
catgagaagc gataacgttt caccataagc aatatattca ttgcaacagt ggaattgcct      120
tatgcgtcaa ggaaggatag atcattgacg gactgagttc aaaaagagac tcgtctaaaa      180
gattttaaga aaggtttcga t                                               201
```

```
<210> SEQ ID NO 21
<211> LENGTH: 293
<212> TYPE: DNA
<213> ORGANISM: Zymomonas mobilis

<400> SEQUENCE: 21
ggtcgaatgc attcctttcg ttacagatat attccgctat aaaactatag aatataagtt      60
atgttccatt cgcagaatag atatagatca gcctctatgg atatgctata tatcgcccat      120
tccatttaag aataataata aaccatcatg ctgtttattt aatattttta ttacagtgaa      180
ttgaagaaat atttcttga taaaaattat taaaaatcta tcaccgacga tccgtctcta      240
tttcaagata gataataatt tgtttaacct gttgattatg cgagataatt tta            293
```

```
<210> SEQ ID NO 22
<211> LENGTH: 145
<212> TYPE: DNA
<213> ORGANISM: Zymomonas mobilis

<400> SEQUENCE: 22
ttaaacttgc tttggctgaa tccttttgtc tttttagat aagtcttaac caattatact       60
```

```
ttttgtttac aacgatggta taaagcgggc ggacaggcta aaaacaggct aaaaggattc      120
ggcctctgtt ttaaggacga gaata                                           145

<210> SEQ ID NO 23
<211> LENGTH: 708
<212> TYPE: DNA
<213> ORGANISM: Zymomonas mobilis

<400> SEQUENCE: 23
aatccaaaat atagaaaaga aggtctgcct ttttatttcg gatactgttt tctgaattgt       60
atttattaca attcagaaaa cgaatattca aaatcgcagc attgcgataa taaattccaa      120
ttaaatggca ataagattg  ctaaatttag tatcgaaaag cgtagaaaac tatcgcttat      180
gcaataaaaa taaatgtttc atgacaacgt tgacaaaaaa actttttattt ttttcataaa    240 aaaacacgaa tgacacaaaa gagaattatt taaagacaga aaaacacaa aaaaaataac      300 aaatattac  cattcctaaa gaaggacttc tttggacaaa agaaattta  tcttagattc     360 aagatatcca aattattttt gaaaaaaaat aaaatacatc caatcccgaa tttatttcgt     420
tttaaatatc agcaaaaata tattttttc  tttatttttt aaaaaataac ttcattttac     480 tttaaattt  ccaagaaaat atttcgaaaa tattttgat  atctttctta attaagaaag     540
aaaacttagt tataatccta ccagttggac gaatcgcaga cggtcgattt cgatttattc     600
aaaaggcctt ttggcacaga agaaaaatcg aggtcatcgt cataatttaa agcgaatgga     660
cagcatatac ctccgtatta cgggggggatt tgtgagtgg  tgagaata                 708

<210> SEQ ID NO 24
<211> LENGTH: 201
<212> TYPE: DNA
<213> ORGANISM: Zymomonas mobilis

<400> SEQUENCE: 24
atcgaaacct ttcttaaaat cttttagacg agtctctttt tgaactcagt ccgtcaatga      60
tctatccttc cttgacgcat aaggcaattc cactgttgca atgaatatat tgcttatggt     120
gaaacgttat cgcttctcat gcgattctat agttaggata aactgattat tgttacgtat     180
tgagtaactg gagtatagac a                                               201

<210> SEQ ID NO 25
<211> LENGTH: 627
<212> TYPE: DNA
<213> ORGANISM: Zymomonas mobilis

<400> SEQUENCE: 25
actttattat attgctcatc tttgttaaaa attatgtatc gataaaagat aaatatcatt      60
tatcttttat cgatattttt tgattttgtc tttgcgtcca gaaaagacag cattccttct     120
caataaagaa atattatttt ttgttttga  aaaattttc  caaatctag  aatgctacat     180 taaatataca aaaatattat tatacaaata aggctttaa  atacccatat ttttagaat     240 ttctttacaa agaaacatgt taaatataga tttagagatt aatatcagcc attttatca     300 aaaattcttt ttttgtttta taatattatg ctgcaaaact aataaaaacg ccctttcgaa     360
attaacgatc acccacaaga aataattatc tgacagcgct taccaatcaa ttattgccga    420
acgcagagtc ccgtattagg acggtcaaca atctaaaccg ttttcagaa  aatattgctt    480 tataagcctc aaaacttaaa agctgcggta ttttaatata ccaaaatttt ctggaaaagc    540
```

```
cggcgaatca gataacagtt ccgcacaggt gagaaccacg acggatcttc tctgaattgt    600
tggttagtta agaaagaaac aaggatt                                        627

<210> SEQ ID NO 26
<211> LENGTH: 302
<212> TYPE: DNA
<213> ORGANISM: Zymomonas mobilis

<400> SEQUENCE: 26
tcagtggtga tcggtgttgc cgaggctgga aagaaatttc aacccgtcc tttccagtta     60 gtgacagggc gcgtttggaa aggctctgct ttcggcggcg ttaaaggcag aaccggtgtt   120
ccgaaaatcg ttgactggta tatgaagggt aaaattgaaa ttgatccgat gattacccat   180
atcctgtcat tagaagagat caataaagcg tttgacctga tgcatgaggg taaatccatt   240
cgttcggttg ttcttttctg attacctgtc ctgttaacct gtggatatag aaggtcggtt   300
ta                                                                  302

<210> SEQ ID NO 27
<211> LENGTH: 398
<212> TYPE: DNA
<213> ORGANISM: Zymomonas mobilis

<400> SEQUENCE: 27
tggcaggata agtgaaagaa aatgggtgtt cacaaaattg ccctagcatg acagaataaa    60
attctttata tcctatcgtg gaaacactgc atgaaagatc gattctgatc aatgtaaggt   120
ttccatttcg taaatggcg taattttgtt agcggaaaga tgctttccgt tgacccttgc    180
cgttatcgtc gctatagcgc ccgtctacat ctcctgttga cggtgaatct ttggcgtcag   240
acgggtgcgc ttgaacattg ccatatatgc gcgtcttcct tttaaagaat tcacgcaggc   300
gagcttagtc atttttgctc ggtgctattt tcataattta attatggtca ggcgcatttt   360
gtatatttgg taaagtaact cttgaggtga agggcttc                           398

<210> SEQ ID NO 28
<211> LENGTH: 1183
<212> TYPE: DNA
<213> ORGANISM: Zymomonas mobilis

<400> SEQUENCE: 28
aaaaatatat cccccgttg aatcattgtt tccaaaacag catcatctta ctgattttg      60 tttaaaaaca acaagattg tctcgtcgag actgtaaata gataaaatat ccgcttccac    120
ataaaagcgg caaaaatttt caaaatttct tttatttttt cattaccgct gcaattttt    180 ttgtcttttt gcgttttttg aggaaagcct gatctgccat tttgagcaga agaaagaaca   240
agctgctttt gatgcagcgt ttgagacaat tgattagatc aaaaatggaa acgataattt   300 tcttttttt ctatttttat tatggatgaa tatccctatt tcggcagagc gggtggcggt    360
agcacttccc cccctcctc ctcaagctac cgcgaccccc atagcttctt ttcctgacta    420 ttccctgca tccttacaaa ttattctttt atttctttt cacaatctat ttggatatct     480
gaaaatgtct ttatttaat gttgtgcaat ttatacagta tatttcgcca tatacgatat    540
tttcttgttt tctatttaca atttggcttt taatatttga acaataaatt ggaatgaata   600
cctaacaact atgttatttt tagtcttatc tttctctaaa aagcctcaaa acgaacaaaa   660
ataacagatt cttcaaaatt tcctttctta aaattttaaca taaatgtttt atttttaaaat 720 atttcgcctg aaatttatta ttttaattta aaggcaaaat cggtaaccac atctcaatta   780
```

```
ttaaacaata cttcataata aaaagacaac ttttttcataa tttgcataag tcttgatgta      840
aaaaatacat atttagaaag aacaagcagc cttgctcatc accgctgtcg cgagtagaaa      900
aatctcggct ttcagaaaat agaggtcgct tcgttaaaca gactataaat gtgctggaat      960
aaagcgaacc ccttgatctg ataaaactga tagacatatt gcttttgcgc tgcccgattg     1020
ctgaaaatgc gtaaaattgg tgattttact cgttttcagg aaaaactttg agaaaacgtc     1080
tcgaaaacgg gattaaaacg caaaaacaat agaaagcgat ttctcgaaaa tggttgtttt     1140
cgggttgttg ctttaaacta gtatgtaggg tgaggttata gct                        1183
```

<210> SEQ ID NO 29
<211> LENGTH: 153
<212> TYPE: DNA
<213> ORGANISM: Zymomonas mobilis

<400> SEQUENCE: 29

```
ttgacgtgaa tagttttatt cttttaaggc cgtcctctac ctttgctgtt tttaaattca       60
cttagatttt tagccttttcc cttatcaagg ctacaaactg aaccatgaca atcatcgcga     120
ttggatcatg gggtttcgaa aaggaaataa agc                                    153
```

<210> SEQ ID NO 30
<211> LENGTH: 433
<212> TYPE: DNA
<213> ORGANISM: Zymomonas mobilis

<400> SEQUENCE: 30

```
taattacgct tttcaaggct gagacaaaat aacagcgctt tcctttagaa aaaaatgcgc       60
tctcttgttt ttatcggaag ttttttcggga ttttcttgaa aagtctctga taatagccac     120
tattttggca gaagaggtct gaaacctctt ttgccatttt tgtttttttta tgctttattt    180 tatcgatttt tttgaatttt cgatttgtgc taatcggtta gcgccacctt gcatcccatc     240 cgccccccctg ctaattaaac tgcggatcat aactggtgaa aatgattgaa aagccttcgg    300
gtttccatct tttattctcg ccggttttgt atgcctatgc ggcatatcca gtgtggccct     360
atgtgcgccc cggttgtttc gaaccgggac ggaatacagg gtgaggcatc tataatctgg     420
ggacggcagg cgc                                                         433
```

<210> SEQ ID NO 31
<211> LENGTH: 534
<212> TYPE: DNA
<213> ORGANISM: Zymomonas mobilis

<400> SEQUENCE: 31

```
cacccaatcc cttgaagact taaactttta gaaaacaata tggggagata ataataaatc       60
gcaatcgctg agcgcccagt taagagagat taacaatctc aagacacact cattcctatg     120
gagattccgc tctcaatgaa gcgctaaaag cagaatattt cctactttc ttctcaaaat       180 catagaatca gcctatcggc ctataaatcg aaaaaatggc ttaaaaatca cgctttccga     240
taaaaacatg agaaaattgt taaattcgga ggaaaaattc attttttctt gcagcatctg    300
gtgaataagc gctttgggca atattgccat ttttgtcagg gaatataaga gtcaccagct    360
taagacgctg cgatccccgc tcgtctagtt gctcaaagga aggacaggat gccggaatta    420
agattataga caaggctccc atcttttctta atgtagcgac caccgccggg attcatttct    480
gacaggaatg aatcttaaaa attttttctat ttattaatgc cataggatca cgac          534
```

<210> SEQ ID NO 32
<211> LENGTH: 96
<212> TYPE: DNA
<213> ORGANISM: Zymomonas mobilis

<400> SEQUENCE: 32
agccttcaaa gggctggaat attttcagcc cttacctctc tccaagggga taaacggaca    60
ggctccatta tccctatttt atatatcggg taacta                              96

<210> SEQ ID NO 33
<211> LENGTH: 133
<212> TYPE: DNA
<213> ORGANISM: Zymomonas mobilis

<400> SEQUENCE: 33
tgattatatg aaaaatatta gaggacgcaa tcttttaat aaaaaatagg ttatattta      60 tataatcctt gcgagaagtt tggcgtaact gtaacaacaa tacgtttgaa tgcgcgggat   120
agaggaagcg ctt                                                      133

<210> SEQ ID NO 34
<211> LENGTH: 151
<212> TYPE: DNA
<213> ORGANISM: Zymomonas mobilis

<400> SEQUENCE: 34
tgctgcaccc gtcgtatgat tcctttgtca ggacaacagg gaaatattta tcctgttgct    60
gtcttgataa acagatgaaa agtgaaaaag taatcatcct cattgataaa tttttataat   120
gagatgtaat tcaatcgctt ttcctagcaa t                                  151

<210> SEQ ID NO 35
<211> LENGTH: 112
<212> TYPE: DNA
<213> ORGANISM: Zymomonas mobilis

<400> SEQUENCE: 35
aacttctgct ataaccaata agctttccct ttgcgagccg cattaacata ttccgttttt    60
ggattcggaa tatctgccgc atcagaggaa agaggaaaag gacggactga aa           112

<210> SEQ ID NO 36
<211> LENGTH: 85
<212> TYPE: DNA
<213> ORGANISM: Zymomonas mobilis

<400> SEQUENCE: 36
aagacgaaaa tatttcttac attgccccca tctcaaagac agtccgcctt tcaaaataga    60
tatcacaaaa tcgggaaaca gaatt                                         85

<210> SEQ ID NO 37
<211> LENGTH: 75
<212> TYPE: DNA
<213> ORGANISM: Zymomonas mobilis

<400> SEQUENCE: 37
attttgcgtg cgatcgctat cccatgatga atagggattg cttcgatatt tttaaaaaat    60
tgggaataaa ctcaa                                                    75

<210> SEQ ID NO 38
<211> LENGTH: 83

<212> TYPE: DNA
<213> ORGANISM: Zymomonas mobilis

<400> SEQUENCE: 38
aagcgttaaa tttcttttcg tctcttgaag accggaaata aaaggccaga ttttacagat    60
ggatagttgg ggagtgccgc ttg    83

<210> SEQ ID NO 39
<211> LENGTH: 322
<212> TYPE: DNA
<213> ORGANISM: Zymomonas mobilis

<400> SEQUENCE: 39
attcaatcaa gtattatttc aacaagggga aagattgctt gctgtaattt ttggatatca    60
aacaggcgaa aaaatgaaag agcgcagcct cttcaaagg caattcgatt tagtccggtg    120
gcattctcac gccacaaacc aaatcataaa taaccgcctc ttttccgcca gataactgca    180
aaattataga acactgacag gctggaatat cgtcattttt cctagacgta atatttccaa    240
aacaagcaat catcgaactt aatcattgta aaccgctatt tgtatcatag caggatcggg    300
aaatatttta aggggggacg gg    322

<210> SEQ ID NO 40
<211> LENGTH: 148
<212> TYPE: DNA
<213> ORGANISM: Zymomonas mobilis

<400> SEQUENCE: 40
ttcattttct tggtctttat gcgacccgct ataaaatccc atatcaacag ccccattgcc    60
tttaggctgt ctgttttgcc ttatttcccg tgataaaagg gctatagtct gcctttagtg    120 attttttggga atggcagaat aacgatcc    148

<210> SEQ ID NO 41
<211> LENGTH: 127
<212> TYPE: DNA
<213> ORGANISM: Zymomonas mobilis

<400> SEQUENCE: 41
gctttctgcg ctcctcacca tttttatggcc gcaatcacca ttcaaaagta accatccacg    60
gagacgccga atcttatga ccgtgcgtcg ttattttcgg gctatagctt tgcggagtaa    120
ataggtc    127

<210> SEQ ID NO 42
<211> LENGTH: 194
<212> TYPE: DNA
<213> ORGANISM: Zymomonas mobilis

<400> SEQUENCE: 42
aaggcaattc atcctgacag cagtctttaa gcgaaattta acattaaaaa atacctgacc    60
atattcaaca atgttttaatt tcactccttg aaagaaaaaa atagcgacaa ttttctaaaa    120
aactatcggc aatactggac atcctatttt aatctggtgt ttttatatca tacaaaacag    180
ggtaatataa atag    194

<210> SEQ ID NO 43
<211> LENGTH: 126
<212> TYPE: DNA
<213> ORGANISM: Zymomonas mobilis

<400> SEQUENCE: 43

```
aagaaatact ccgattaaac agggaaata tcaaaaaata tcttttagct gatagatgat      60
atcaagcaaa tgatgaactg tttaaatttt taaaacacga aatagaaaaa ggatggattg    120
ggcgcc                                                                126
```

<210> SEQ ID NO 44
<211> LENGTH: 627
<212> TYPE: DNA
<213> ORGANISM: Zymomonas mobilis

<400> SEQUENCE: 44

```
actttattat attgctcatc tttgttaaaa attatgtatc gataaaagat aaatatcatt     60
tatcttttat cgatattttt tgattttgtc tttgcgtcca gaaaagacag cattccttct   120
caataaagaa atattatttt tgttttttga aaaattttc caaatctag aatgctacat    180
taaatataca aaatattat tatacaaata aggcttttaa atacccatat ttttagaat     240
ttctttacaa agaaacatgt taaatataga tttagagatt aatatcagcc attttatca   300
aaaattcttt ttgttttta taatattatg ctgcaaaact aataaaaacg ccctttcgaa   360
attaacgatc acccacaaga ataattatc tgacagcgct taccaatcaa ttattgccga   420
acgcagagtc ccgtattagg acggtcaaca atctaaaccg tttttcagaa atattgctt    480
tataagcctc aaaacttaaa agctgcggta ttttaatata ccaaaatttt ctggaaaagc   540
cggcgaatca gataacagtt ccgcacaggt gagaaccacg acggatcttc tctgaattgt   600
tggttagtta agaaagaaac aaggatt                                        627
```

<210> SEQ ID NO 45
<211> LENGTH: 364
<212> TYPE: DNA
<213> ORGANISM: Zymomonas mobilis

<400> SEQUENCE: 45

```
tgtgttctcc tgctacgaga acactttaat tctaaaatat attttgatt agatatataa     60
ttaaaaagat agttatgaat atgattcatg aatattttt gagattaaaa atcctctatt   120
tgaatagta ttattaggct tgttattaa cggatattgt tatttataga gattaagcag    180
gccatttcaa aaatatcgag atgatgcgct ctctatcaat tttgctttc tctctctgtt   240
ccacgtgaaa caaaaggcc gcattccgac aaattacagg ctcttttcag cttaaaaca    300
aggttgatga ttgtttttca tcccgaaaac tgtttgatag ctttttctg tttctcccgt   360
ctgg                                                                 364
```

<210> SEQ ID NO 46
<211> LENGTH: 104
<212> TYPE: DNA
<213> ORGANISM: Zymomonas mobilis

<400> SEQUENCE: 46

```
ttcgtctatt ccaaagagat ttattcaaat atcactataa aataggtcgc ttcgggatag     60
aaaacagtcg gtcttcccta ttttaatttg atcaaggtat tcca                    104
```

<210> SEQ ID NO 47
<211> LENGTH: 338
<212> TYPE: DNA
<213> ORGANISM: Zymomonas mobilis

<400> SEQUENCE: 47

```
cgggtttagg actcctgcaa aaaaaggctt tgtttcggat cggataaaag gattaaacgg      60
attcatccat cgttatgttt aattttagat tttttatccc tgaatagcga ggggtataca     120
tcactgtttt ttgggaaaaa acggcggtga aattcctatt tttctgtagc gctttgtgaa     180
gcttttctgg gatatttggc ttttttgcct tgttcttatc gtattttttg ggttttttacc   240 ggaaaatgct ctgatgctat atcggttttg tgcttttttcc cgacttttcg ggctttgttc   300
cgaaatatcg ggaaaatcgg ttggaaatca ggaaaaaa                             338
```

<210> SEQ ID NO 48
<211> LENGTH: 106
<212> TYPE: DNA
<213> ORGANISM: Zymomonas mobilis

<400> SEQUENCE: 48

```
aggggaacc tttcagtgac caaggcacaa atagtgccg gattgcggat aatttccaga       60
acagacatgc tcctgacaga agcttgttga aaaggaaata tcaatt                   106
```

<210> SEQ ID NO 49
<211> LENGTH: 293
<212> TYPE: DNA
<213> ORGANISM: Zymomonas mobilis

<400> SEQUENCE: 49

```
aaaatatcca tcaaggctcg acgtaatctg cttcaaatca gaaatttaac aaggcctata     60 tttttttatta gaccgtctat gtctttaatt tttgaaaaat actaccgcca gaccacaaaa   120
tatgtctcac atgggttgtt ttaaaaattt tcattaccca aaaattgaaa tttgctttct   180
tttaatgtga taacagggt tttagcctga aatcatttga ccttgctttc cctatttcat    240
tccgctttaa agcttccatt ttgaagcata tttgaatgat aaaggcagga ttc           293
```

<210> SEQ ID NO 50
<211> LENGTH: 208
<212> TYPE: DNA
<213> ORGANISM: Zymomonas mobilis

<400> SEQUENCE: 50

```
tatcttcctt cagaatttga gacgctgcct tgtcagatgg tctgcaatgc cgtctcctaa    60
aagtaaagac agccttgcga taatataact gccagataaa tccggctatc aagataaaag  120
ccaagctcga ccttaatttta cggagattac cggaaaaaat cgaacgaaa gagttgaact   180 ctgcttttga ccgattatgc catgagct                                        208
```

<210> SEQ ID NO 51
<211> LENGTH: 371
<212> TYPE: DNA
<213> ORGANISM: Zymomonas mobilis

<400> SEQUENCE: 51

```
aaacggttac tgggctttag ctgccttgta aaaggtatct tcatagcctt aaaaacagaa     60
aaaccggcct gattttttcag gtcggttttt tattacttta acttcgatta tatcgcagat  120
tttagaaaga atgacgcgct tgagtttcgc aaattcaaag ctaccctgac attatctaac   180
tctcaattct tatctcacag cgataatttc gccccagaaa actgctctaa gcacactgcc   240
tacgaaaaat ccaaaatcac tataaaggcc aagcctgcgg cttcctata aaaccattc     300 ttacctttag gatctggctg tcccgttcta tcattagact ttcattctac gtcaaaaaag   360
```

```
gggaggggggt a                                                          371
```

<210> SEQ ID NO 52
<211> LENGTH: 270
<212> TYPE: DNA
<213> ORGANISM: Zymomonas mobilis
<400> SEQUENCE: 52

```
gtaaattggc ctaaccgcct tttaaaaaat caccctgaaaa ggacagccgg ctttaaatat     60
tttaaatgcc ggccaaaggc gttttaccta aactttaggg cagtaaagaa aagctaactg    120
tcctttcaaa gatagggggct gctaagtcct attcaaaatc aaaggcttgc ctctctattt    180
actttcaggc ttcgttgaat gaacagagat agagctgcaa tctgcgacaa aactggataa    240
taggttaggg gctctgttcc aaaggttgtt                                     270
```

<210> SEQ ID NO 53
<211> LENGTH: 40
<212> TYPE: DNA
<213> ORGANISM: Zymomonas mobilis
<400> SEQUENCE: 53

```
ggcatgttcg cggccgccgg ttccgataag caggacgttc                            40
```

<210> SEQ ID NO 54
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 54

```
tgggaataaa ctcaagcccc tgcatcgcag g                                     31
```

<210> SEQ ID NO 55
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 55

```
gcccttgctc accatgcccc tgcgatgcag g                                     31
```

<210> SEQ ID NO 56
<211> LENGTH: 19
<212> TYPE: DNA
<213> ORGANISM: Artificial Sequence
<220> FEATURE:
<223> OTHER INFORMATION: The sequence is synthetized.

<400> SEQUENCE: 56

```
gccctgcat cgcagggggc                                                   19
```

<210> SEQ ID NO 57
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 57

```
gcgtcgtcgc ctttgcgacg gcgc                                             24
```

```
<210> SEQ ID NO 58
<211> LENGTH: 30
<212> TYPE: DNA
<213> ORGANISM: Artificial Sequence
<220> FEATURE:
<223> OTHER INFORMATION: The sequence is synthetized.

<400> SEQUENCE: 58
ggaagggtat agatatatcc atatccttcc                                       30

<210> SEQ ID NO 59
<211> LENGTH: 25
<212> TYPE: DNA
<213> ORGANISM: Artificial Sequence
<220> FEATURE:
<223> OTHER INFORMATION: The sequence is synthetized.

<400> SEQUENCE: 59 gccgggggggg acatttctct ccggc                                           25

<210> SEQ ID NO 60
<211> LENGTH: 28
<212> TYPE: DNA
<213> ORGANISM: Artificial Sequence
<220> FEATURE:
<223> OTHER INFORMATION: The sequence is synthetized.

<400> SEQUENCE: 60
tttcgaggtg gcttcggcca cctcgtca                                         28

<210> SEQ ID NO 61
<211> LENGTH: 33
<212> TYPE: DNA
<213> ORGANISM: Artificial Sequence
<220> FEATURE:
<223> OTHER INFORMATION: The sequence is synthetized.

<400> SEQUENCE: 61
ggtcaacttc tctcaaaata ggagaagttg gcc                                   33

<210> SEQ ID NO 62
<211> LENGTH: 198
<212> TYPE: DNA
<213> ORGANISM: Artificial Sequence
<220> FEATURE:
<223> OTHER INFORMATION: The sequence is synthetized.

<400> SEQUENCE: 62
gatcatttca caaaaaatga gaaaaaatta aggatgagtc cttctttgta aaaggagga       60 ctgtcctaag ctgaagtaat aagaaggta ggctctttta tggcatatga atctgtcaat      120
cccgccactg gcgaaaccgt caaaaatat cctgattttt ctgataaaca ggttaaagat      180
tccgttgatc gggcggcg                                                  198

<210> SEQ ID NO 63
<211> LENGTH: 53
<212> TYPE: DNA
<213> ORGANISM: Artificial Sequence
<220> FEATURE:
<223> OTHER INFORMATION: The sequence is synthetized.

<400> SEQUENCE: 63
atggtattga tgtttgatca tttcacaaaa aatgagaaaa aattaaggat gag             53

<210> SEQ ID NO 64
```

<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 64
gcccttgctc accatcgccg cccgatcaac g            31

<210> SEQ ID NO 65
<211> LENGTH: 25
<212> TYPE: DNA
<213> ORGANISM: Artificial Sequence
<220> FEATURE:
<223> OTHER INFORMATION: The sequence is synthetized.

<400> SEQUENCE: 65
aaacatcaat accataacga agacc                   25

<210> SEQ ID NO 66
<211> LENGTH: 280
<212> TYPE: DNA
<213> ORGANISM: Zymomonas mobilis

<400> SEQUENCE: 66
cacgagctca gaagttttct gcattgtctc cgaattcctt gccctgcttt ctgtggcaaa     60
gggattcaga aattaaaccc tacgaaaacc acaatgcctc cgaagcccat ttcggaggca    120
ttatgtttca gtcttattgg gctgtcagct ttttggccaa ttcggccaca tgcttgccta    180
agaatttcgc gccatccaac tcattcttgc taggctgccg tgaaccatcg cttgcggcaa    240
tggtcgtcgc gccatagggc gcaccacctg ttacttcatc                         280

<210> SEQ ID NO 67
<211> LENGTH: 304
<212> TYPE: DNA
<213> ORGANISM: Zymomonas mobilis

<400> SEQUENCE: 67
tttttctttt tcaatcaact ttaatgatga aaaaaaatac aaaagaagtt tttatcaaaa     60
gagcgggata gggggatttt ggtagccgtt ttttttacaa gacaagaatg agagagtggt    120
tcgcaactaa tgttgcatct ataacacatt tctcgcccat tttagcacag acatgaaaag    180
cacgatgaca agatcgcaga agtcgcatag ccttcaatac aggccttaat tcaaggggga    240
ttggtctaaa agactaaagt ctttttatga ttctttcggg gggaagtaat caaaagacta    300
tatg                                                                304

<210> SEQ ID NO 68
<211> LENGTH: 198
<212> TYPE: DNA
<213> ORGANISM: Artificial Sequence
<220> FEATURE:
<223> OTHER INFORMATION: The sequence is synthetized.

<400> SEQUENCE: 68
gatcatttca caaaaaatga gaaaaaatta aggatgagtc cttctttgta aaaggagga     60
ctgtcctaag ctgaagtaat aagaaaggta ggctctttta tggcatatga atctgtcaat    120
cccgccactg gcgaaaccgt caaaaaatat cctgattttt ctgataaaca ggttaaagat    180
tccgttgatc gggcggcg                                                 198

```
<210> SEQ ID NO 69
<211> LENGTH: 277
<212> TYPE: DNA
<213> ORGANISM: Artificial Sequence
<220> FEATURE:
<223> OTHER INFORMATION: The sequence is synthetized.

<400> SEQUENCE: 69
ctgcttttgc agagcaaaaa caagcattgc tttatatcta tcccgaagcg ggtcacggtt      60
ttgcgaccga aaagggaaa agacgcgctg aaaaatcggc cgaattggcc gatcagcgga     120
gtctcgattt tattgaaagg aatttatgat gagtgaagcc tatgcgatta tcgctgaaaa     180
agccggaggc cctgaagttc tggtcaagaa accgcttgat cttggcaaga tgaagccaga     240
agcaggccaa gttttattac ggcatcaggc tattggt                             277

<210> SEQ ID NO 70
<211> LENGTH: 221
<212> TYPE: DNA
<213> ORGANISM: Artificial Sequence
<220> FEATURE:
<223> OTHER INFORMATION: The sequence is synthetized.

<400> SEQUENCE: 70
gaaaaaggct ggtcaaccct tggaaccaat caagcctctg gccaatatac cgcattccct      60
attgcgcccc gtatgttctt catcacggtt caggccggtt tctaattttc gaggcttta     120 ctatgacccg cttcaatcgc cgccattttc tacaaactac aggcgctctt cttggcagca     180
gtagcctctt aaaaggaaca gaccttttcg cggctcccag c                        221

<210> SEQ ID NO 71
<211> LENGTH: 168
<212> TYPE: DNA
<213> ORGANISM: Artificial Sequence
<220> FEATURE:
<223> OTHER INFORMATION: The sequence is synthetized.

<400> SEQUENCE: 71
aagatgatgc ttctttcaag accaagtgcg cagaccaaat ccaacgatta agagtattga      60
gtgaaacata tgtctgctga attcagcgaa tttgtcttgt tctccgaaga agaaatccgt     120
gcgctcgacg cgcgagttac tctgcgagag agtcggggaa aacaggtg                 168

<210> SEQ ID NO 72
<211> LENGTH: 99
<212> TYPE: DNA
<213> ORGANISM: Artificial Sequence
<220> FEATURE:
<223> OTHER INFORMATION: The sequence is synthetized.

<400> SEQUENCE: 72
atgactgaaa gctctattca cgatcccctc accattcgtc gcctctatgg cagacaacaa      60
ggccacagcc tgcgcccgaa acaggcagaa ttagtggaa                            99

<210> SEQ ID NO 73
<211> LENGTH: 200
<212> TYPE: DNA
<213> ORGANISM: Zymomonas mobilis

<400> SEQUENCE: 73
ccttttttct cctgccacat gaagcacttc actgacaccc tcatcagtgc caacatagta      60
agccagtata cactccgcta gcgcaaataa taaaaaagcc ggattaataa tctggctttt     120
```

-continued

```
tatattctct ctctagtata taaacgcaga aaggcccacc cgaaggtgag ccagtgtgac      180
ctgcagcggc cgctactagt                                                  200

<210> SEQ ID NO 74
<211> LENGTH: 46
<212> TYPE: DNA
<213> ORGANISM: Zymomonas mobilis

<400> SEQUENCE: 74
caaataaaac gaaaggctca gtcgaaagac tgggcctttc gtttta                     46
```

METHOD FOR CHARACTERIZING BIOLOGICAL PART BASED ON DUAL-FLUORESCENT REPORTER GENE SYSTEM AND BIOLOGICAL PART LIBRARY CONSTRUCTED THEREON

CROSS REFERENCE OF RELATED APPLICATION

This is a U.S. National Stage under 35 U.S.C. 371 of the International Application PCT/CN2019/086173, filed May 9, 2019, which claims priority under 35 U.S.C. 119(a-d) to CN 201910114635.7, CN 201910114932.1 and CN 201910114652.0, all filed Feb. 14, 2019.

BACKGROUND OF THE PRESENT INVENTION

Field of Invention

The present invention relates to a technical field of biology, and more particularly to a method for identifying biological parts based on a dual-fluorescent reporter gene system and a biological part library constructed thereon.

Description of Related Arts

*Zymomonas mobilis* (*Z. mobilis*) is the gram-negative and facultative anaerobic bacteria, which is peritrichous and has a size of (1.4-2.0)*(4.0-5.0) µm. An appropriate growth temperature of *Z. mobilis* is 30° C., and a tolerant pH range is 3.5-9. *Z. mobilis* can high-efficiently utilize the glucose, fructose and saccharose to generate ethanol through the ED (Enter-Doudoroff) pathway. Because of the advantages of high ethanol yield and tolerance, high osmotic pressure tolerance, low biomass, and no need of adding oxygen when fermenting, *Z. mobilis* has become one of the main strains for producing the bio-ethanol. In order to improve the application range of *Z. mobilis*, the system biological researches on *Z. mobilis* are carried out successively. Meanwhile, with the development of metabolic engineering and synthetic biology, the demands on the available biological parts in *Z. mobilis* are increasing.

However, at present, mining of the system biological data of *Z. mobilis* is still not enough, and particularly there are fewer researches about mining and development of the biological parts such as the promoters and the ribosome binding sequences in the genome scale, causing that the identified available biological parts of *Z. mobilis* become fewer and fewer, which greatly limits the developments of the accurate metabolic engineering on *Z. mobilis* and the synthetic biology era.

The promoter is the important part for regulating the gene expression and is the site can be identified and specifically bound by the RNA polymerase. The intensity of the promoter is generally used for describing the initial transcription frequency of the RNA polymerase at the promoter. When conducting the biological synthesis, the promoter of certain intensity is selected for assisting the successful completion of the biological synthesis.

The conventional promoter screening method is to randomly cut the genome, and then identify whether the obtained sequence is the promoter sequence and how is the intensity thereof through the expression of the downstream single reporter system. The conventional detecting system is generally the single-reporter gene system. However, the expression of the reporter gene in the single-reporter gene system will be influenced by multiple factors from the internal and external of the strains, which influences the identification of the system to the promoter. Moreover, with the conventional method, the speed of obtaining the promoter to be detected is slow, and the intensity identification cannot be conducted with fast speed and high throughput, which is unbeneficial to the high-efficient quantitative research of the promoter. With the development of the various technologies, although some new methods are developed, such as the in vitro detecting techniques of electrophoretic mobility shift assay and atomic force microscope, the applications of these methods are limited due to the low accuracy.

In conclusion, it is urgent to develop and mine the biological parts available for metabolic engineering of *Z. mobilis* with the conventional system biological data, especially the promoters and the ribosome binding sites of certain intensities and sRNA-UTR interaction pairs, and to establish an in vivo quantitative analysis method for the promoters and other biological parts with high efficiency, fast speed and high throughput, which is significant for expanding the part library of promoters of *Z. mobilis* and other biological parts. Moreover, the method can also be applied in other microorganism systems, and provide various biological functions and regulation parts for metabolic engineering and synthetic biology.

SUMMARY OF THE PRESENT INVENTION

Aiming at existing problems in prior art, the present invention provides a method for identifying biological parts based on a dual-fluorescent reporter gene system and a biological part library constructed thereon.

The above technical object of the present invention is realized through technical solutions as follows.

A method for identifying biological parts based on a dual-fluorescent reporter gene system comprises steps of:

(S1) with pEZ15Asp plasmids as a skeleton, constructing a single-fluorescent reporter gene system, and screening fluorescent proteins;

(S2) according to expressions of different fluorescent protein genes in *Zymomonas mobilis* (*Z. mobilis* hereinafter), screening suitable fluorescent reporter genes, respectively named as a first fluorescent reporter gene and a second fluorescent reporter gene; choosing suitable promoters for the first and second fluorescent reporter genes, respectively named as a first promoter and a second promoter;

(S3) with pEZ15Asp as a template, respectively designing a forward primer and a reverse primer, conducting PCR (Polymerase Chain Reaction) amplification, and obtaining a pEZ15Asp skeleton;

(S4) with utilizing a modified Gibson assembly method, connecting first promoter-first fluorescent reporter gene and second promoter-second fluorescent reporter gene to the pEZ15Asp skeleton, adding a terminator between the two fluorescent reporter genes, and obtaining the dual-fluorescent reporter gene system;

(S5) with the dual-fluorescent reporter gene system as a template, respectively designing a forward primer and a reverse primer, conducting PCR amplification, and obtaining a dual-fluorescent reporter gene system skeleton;

(S6) through the modified Gibson assembly method, transforming the biological parts to be detected and the dual-fluorescent reporter gene system skeleton obtained in the step of S5 into *Escherichia coli* DH5α; verifying positive clones on a plate by PCR; after culturing overnight, extracting plasmids; and (S7) transforming the plasmids extracted in the step of S6 into ZM4 competent cells; activating and culturing to a logarithmic phase, then detecting and verifying with a flow cytometer.

Preferably, in the step of S1, the fluorescent proteins are all promoted by a promoter PlacUV5; the fluorescent proteins are one of EGFP, mCherry, RFP, CFP, and opEGFP, opmCherry and opCFP after being optimized by a codon.

Preferably, in the step of S2, the first promoter is Ptet; the second promoter is PlacUV5; the first fluorescent reporter gene and the second fluorescent reporter gene are respectively EGFP and opmCherry.

Preferably, in the step of S3, the forward primer and the reverse primer are respectively a first primer and a second primer; sequences of the first primer and the second primer respectively refer to SEQ ID NO: 1 and SEQ ID NO: 2.

Preferably, in the step of S5, the forward primer and the reverse primer are respectively a primer Prtt-F and a primer Prtt-R; sequences of the primer Prtt-F and the primer Prtt-R respectively refer to SEQ ID NO: 3 and SEQ ID NO: 4; or in the step of S5, the forward primer and the reverse primer are respectively the primer Prtt-F and a primer PgapTSS-R; sequences of the primer Prtt-F and the primer PgapTSS-R respectively refer to SEQ ID NO: 3 and SEQ ID NO: 65.

Preferably, in the step of S6, the biological parts to be detected are endogenous promoters of different intensities, promoters containing synthetic RBS (Ribosome Binding Site) sequences of different intensities, terminators of different intensities, or sRNA-UTR (soluble Ribonucleic Acid-Untranslated Region) interaction pairs.

Further preferably, the biological parts to be detected are the endogenous promoters of different intensities or the promoters containing the synthetic RBS sequences of different intensities; the promoters containing the RBS sequences of different intensities are obtained through steps of:

(Sa) according to different omics data, screening out genes having strong downstream expressions; then conducting Venn analysis; and screening out shared genes of each omics data;

(Sb) predicting the RBS sequences of different intensities; and (Sc) with the dual-fluorescent reporter gene system as a template, conducting PCR amplification with a primer pEZ-tetR-F and a primer RBS-R, wherein lowercases at a 5' terminal of each primer are homologous arms of the dual-fluorescent reporter gene system; and obtaining the promoters containing the RBS sequences of specific intensities.

Further preferably, the biological parts to be detected are the terminators of different intensities; the terminators of different intensities are obtained through steps of:

(S01) screening a gene set whose contiguous genes in a same transcription direction have large expression differences, and ordering according to the expression differences;

(S02) with a bioinformatics method, predicting terminator sequences between the contiguous genes, and representing the intensities of the terminators by the expression differences between the contiguous genes; and (S03) designing primers for a target terminator sequence, conducting PCR amplification, and obtaining terminator fragments.

Further preferably, the biological parts to be detected are the sRNA-UTR interaction pairs; UTR fragments are obtained through steps of:

(S0a) with a bioinformatics method, analyzing a target sequence; after determining a transcriptional start site, retaining the sequence from the transcriptional start site to 99-bp after an initiation codon ATG, as a target 5' UTR sequence;

(S0b) with a Z. mobilis genome as a template, designing a forward primer and a reverse primer, conducting PCR amplification, and obtaining the target UTR sequence fragments;

with a dual-fluorescent reporter gene system containing a promoter Pgap as a template, conducting PCR amplification, and obtaining the dual-fluorescent reporter gene system skeleton.

Further preferably, in the step of S7, the plasmids are electronically transformed into the ZM4 competent cells, particularly comprising steps of:

(1) placing the ZM4 competent cells on ice; after the ZM4 competent cells melt, taking 50 µL of the competent cells and adding into an electro-transformation cup, and then adding 1 µg of the plasmids into the electro-transformation cup, wherein electro-transformation conditions are 1600 V, 25 µF and 200 Ω;

(2) after completing electro-transformation, resuscitating at 30° C. in RM (Rich Media);

(3) centrifuging a culture, which is obtained after 6-12 hours of resuscitation, with a rotational speed of 6000 rpm for 1 minute, so as to remove a supernatant;

(4) adding 200 µL of fresh RM; taking a sample of 100 µL and coating on a resistant plate containing corresponding antibiotics; and culturing at 30° C. for 2 days; and (5) conducting PCR positive clone verification with a primer Pdual-F and a primer Pdual-R, wherein:

```
a sequence of the Pdual-F is
CCGCTCACAATTCCACACATTATAC, referring to
SEQ ID NO: 8;
and a sequence of the Pdual-R is
ACCAGGATGGGCACCAC, referring to
SEQ ID NO: 9.
```

Further preferably, in the step of S7, the intensities are detected and verified with the flow cytometer, particularly comprising steps of:

(1) activating and culturing mono-clones, which are loaded into the dual-fluorescent reporter gene system and verified to be correct by PCR positive clone verification, in RM containing corresponding antibiotics;

(2) after culturing to the logarithmic phase, taking a sample of 200 µL; centrifuging with a rotational speed of 12000 rpm for 1 minute, so as to remove a supernatant; washing with 1×PBS (Phosphate Buffered Saline) for two times, and re-suspending;

(3) detecting with the flow cytometer, wherein a cell collection event is set to be 20,000.

A second object of the present invention is to provide a biological part library constructed on the method for identifying the biological parts based on the dual-fluorescent reporter gene system.

Compared with the prior art, the present invention has beneficial effects as follows.

With the Z. mobilis as the type strains, the present invention establishes the method for predicting and screening the promoter sequences of different intensities with utilizing the system biological data. The predicting and screening method is high-efficient and quick, and can serve as a guidance basis of the experiments. The present invention integrates the existing system biological data, and high-efficiently and quickly screens the promoters of specific intensities. The RBS intensities and the promoter intensities, predicted and screened by the present invention, have the relatively good correlation with the experimental data (respectively $R^2>0.9$ and $R^2>0.7$), illustrating that the method for screening the promoters based on the system biological data, provided by the present invention, can be applied in predicting and screening the promoters and other biological parts of different demands. Compared with the conventional promoter screening and identifying method, the method provided by the present invention can screen and quantify the promoters of different intensities and other biological parts with fast speed and high throughput, and the quantitative analysis of the promoters is completed inside the cells, which is less influenced by the internal and external environmental change of the cells and is accurate; moreover, the method provided by the present invention can quickly expand the biological part library of Z. mobilis, so as to be applied in metabolic engineering of different demands.

According to the present invention, with the conventional system biological data and the bioinformatics method, the biological parts of different intensities are predicted and screened, and the intensities are identified and verified through the dual-fluorescent reporter gene system developed by the laboratory of the inventors, for quantitatively analyzing the intensities of the promoters and other biological parts and finding the biological parts available for metabolic engineering and synthetic biology. Combined with the two methods, a strategy for quickly selecting the stand-by biological parts is established, which is applicable in the rational design of the synthetic biology era and the microorganism modification.

Moreover, the dual-fluorescent reporter gene system provided by the present invention can be applied in the quantitative analysis of other biological parts, and in the other species besides Z. mobilis. The advantages of the present invention are listed in the following table.

Comparison of advantages and disadvantages between present invention and prior art

| Item | Prior art | Present invention |
| --- | --- | --- |
| Promoter screening method | Random test | Omics data analysis |
| Promoter intensity identifying method | In vitro test or in vivo single reporter gene system | In vivo dual-fluorescent reporter gene system |
| System adaptability | Easily influenced by external environment | Hardly influenced by external environment |
| Intensity identification accuracy | Based on phenotype Inaccurate quantization | Detecting fluorescence intensity with flow cytometer Accurate quantization |
| Operability | Complex operation | Easy operation |
| Throughput | Low | High |
| Whether experimental results can serve as prediction basis | No | Yes |
| Applicable part range of system | Limited range | Wide range |

The conventional method for identifying the interactive relationship of sRNA-UTR has the complex operation, and detecting is generally conducted in vitro, which cannot avoid the troubles of obtaining the experimental material in vitro and conducting the related experiments in vivo, causing that whether the interactive relationship exists between sRNA and the target UTR thereof cannot be quickly determined, so that it is unbeneficial to batch operation and cannot be applied in the batch quantitative analysis of the intensity of the interaction between the target sRNA and the target 5' UTR thereof. Compared with the conventional method for identifying the interactive relationship of sRNA-UTR, the present invention is convenient and quick, and has the easy operation. With the dual-fluorescent reporter gene system based on the flow cytometry, the present invention conducts detecting in vivo, which avoids the troubles of obtaining the experimental material in vitro and conducting the related experiments in vivo, is able to quickly determine whether the interactive relationship exists between sRNA and the target UTR thereof, and is beneficial to batch operation. With utilizing the dual-fluorescent reporter gene system, the method provided by the present invention can be applied in quantitatively analyzing the intensity of the interaction and can be transplanted to other species besides Z. mobilis. The present invention provides a method for identifying the interaction between sRNA and the target mRNA 5' UTR thereof, which is able to quickly and high-efficiently determine the interactive relationship between the target sRNA and the target 5' UTR thereof and conducts the quantitative analysis.

With utilizing the common database, biological data and dual-fluorescent reporter gene system, the present invention screens and identifies the intensities of 37 promoters and 4 RBS (Ribosome Binding Site), and the intensities of 4 sRNA-UTR interaction pairs and 6 terminators, which greatly expand the part library of Z. mobilis. The present invention can realize the full mining and utilization of the system biology of Z. mobilis and different microorganism systems and expand the biological part library thereof, and can be applied in metabolic engineering and synthetic biology. The present invention is simple, has easy operation and wide range of applicable biological parts, and can be promoted to other species.

BRIEF DESCRIPTION OF THE DRAWINGS

In FIG. 7, TSS represents transcriptional start site; ATG represents initiation codon; WT represents wild-type strain; ΔsRNA represents target sRNA knock-out strain; and OE_sRNA represents target sRNA over-expressed strain.

DETAILED DESCRIPTION OF THE PREFERRED EMBODIMENT

Technical solutions of the present invention will be clearly and completely described with following preferred embodiments. The described preferred embodiments are merely a part of the embodiments of the present invention, not all of the embodiments. Based on the preferred embodiments of the present invention, all of other embodiments made by one of ordinary skill in the art without creative efforts should be encompassed in the protection scope of the present invention.

The present invention provides a method for identifying biological parts based on a dual-fluorescent reporter gene system and a biological part library constructed thereon. Details are illustrated with the preferred embodiments as follows.

Figure 1A:
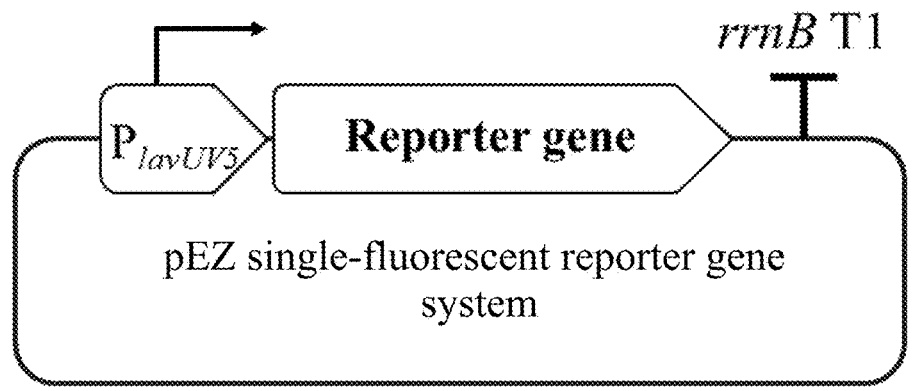
FIG. 1A is a sketch view of a single-fluorescent reporter gene system according to a first preferred embodiment of the present invention.
Figure 1B:
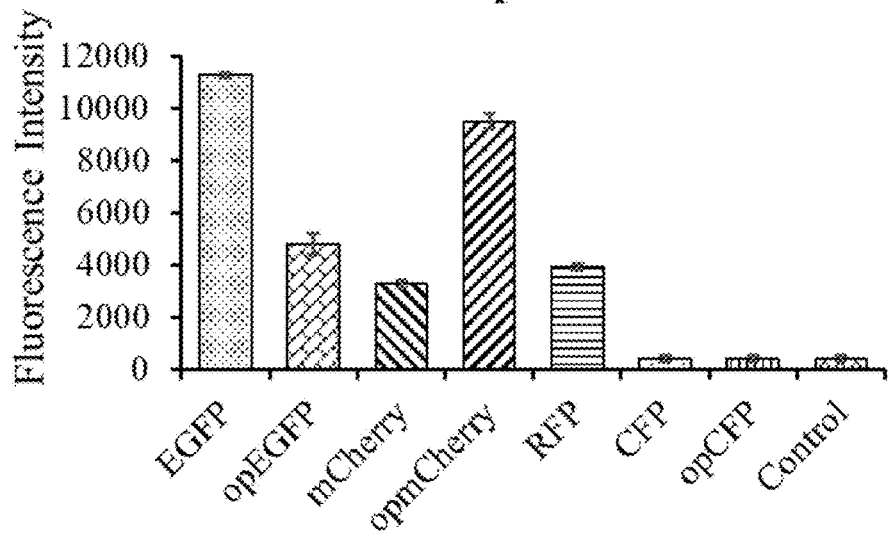
FIG. 1B is a diagram of expression results of screened fluorescent proteins according to the first preferred embodiment of the present invention.
Figure 2:
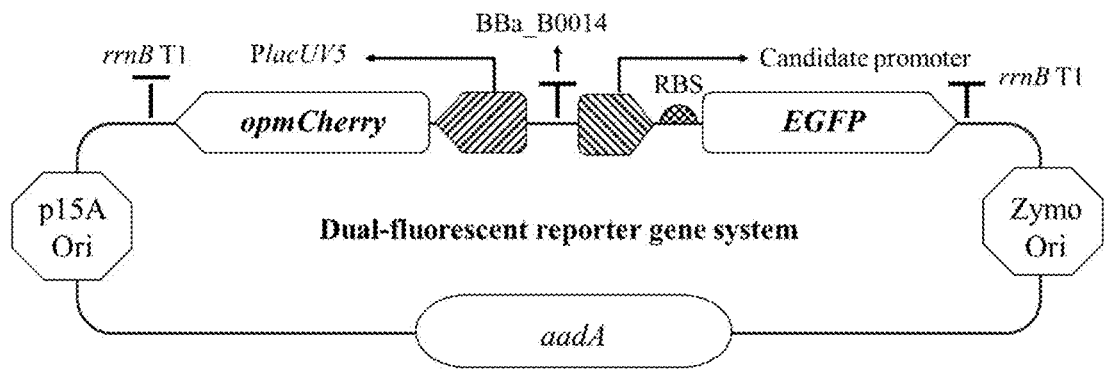
FIG. 2 is a sketch view of a dual-fluorescent reporter gene system according to the first preferred embodiment of the present invention.

First Preferred Embodiment: Method for Identifying Biological Parts Based on Dual-Fluorescent Reporter Gene System The method comprises steps of:

(S1) with pEZ15Asp plasmids as a skeleton, constructing a single-fluorescent reporter gene system as shown in FIG. 1A, for screening fluorescent proteins, wherein: the fluorescent proteins are one of EGFP, mCherry, RFP, CFP, and opEGFP, opmCherry and opCFP after being optimized by a codon; and the fluorescent proteins are all promoted by a promoter PlacUV5;

(S2) sending gene sequences of every fluorescent protein to a third-party company for gene sequence synthesis; with pEZ15Asp as a template, conducting PCR (Polymerase Chain Reaction) amplification respectively with a first primer and a second primer, and obtaining a pEZ15Asp skeleton; with utilizing a Gibson assembly method, connecting PlacUV5-fluorescent reporter gene to the pEZ5Asp skeleton; through transforming into *Escherichia coli* DH5α, obtaining the single-fluorescent reporter gene system; for obtained recombinant strains, verifying positive clones on a plate by PCR, extracting plasmids after culturing overnight, and sequencing for verifying connection and sequence correctness; transforming the extracted plasmids into ZM4 competent cells, activating and culturing to a logarithmic phase, and detecting expression intensities with a flow cytometer; wherein:

```
a sequence of the first primer is
5'-GCGCTAGCGGAGTGTATACTGGCTTACTATGTT-3',
referring to SEQ ID NO: 1;
and a sequence of the second primer is
5'-ACGGTGAGCTGGTGACCTGCCTTATC-3',
referring to SEQ ID NO: 2;
``` according to fluorescent expression intensities of different fluorescent protein genes in *Zymomonas mobilis* (*Z. mobilis* hereinafter), screening suitable fluorescent reporter genes, respectively named as a first fluorescent reporter gene and a second fluorescent reporter gene; wherein: Ptet is chosen as a first promoter, and PlacUV5 is chosen as a second promoter; it can be seen from expression results shown in FIG. 1B that: in the first preferred embodiment, the fluorescent proteins EGFP and opmCherry have relatively high fluorescent expression intensities in *Z. mobilis*; therefore, the fluorescent proteins EGFP and opmCherry are involved in subsequent experiments, respectively as the first fluorescent reporter gene and the second fluorescent reporter gene;

(S3) with pEZ15Asp as the template, designing the first primer and the second primer, conducting PCR amplification, and obtaining the pEZ15Asp skeleton; according to a PCR recovery kit, recovering and purifying a PCR product; wherein:

preparation of a PCR system is:

| Reagent | Volume | Concentration |
|---|---|---|
| first/second primer | 2 μL | 10 μM |
| primerSTAR | 25 μL | 2× |
| template | 1 μL | 1 ng |
| ddH₂O | Up to 50 μL | | setting of a PCR program is: pre-denaturing at 98° C. for 3 minutes, denaturing at 98° C. for 10 seconds, annealing at 55° C. for 10 seconds, and extending at 72° C. for 35 seconds, totally 29 cycles;

(S4) with utilizing a modified Gibson assembly method, connecting Ptet-first fluorescent reporter gene, namely Ptet-EGFP, and PlacUV5-second fluorescent reporter gene, namely PlacUV5-opmCherry, to the pEZ15Asp skeleton obtained in the step of S3; adding a terminator between the two fluorescent reporter genes; and obtaining an inducible dual-fluorescent reporter gene system, as shown in FIG. 2; wherein:

in the first preferred embodiment, the terminator added between the two fluorescent reporter genes is a terminator BBa_B0014, and a sequence thereof is:

```
5'-CCTTTTTTCTCCTGCCACATGAAGCACTTCACTGACACCCTCATCAG

TGCCAACATAGTAAGCCAGTATACACTCCGCTAGCGCAAATAATAAAAAA

GCCGGATTAAIAATCTGGCTTTTTATATTCTCTGECTAGTATATAAACGC

AGAAAGGCCCACCCGAAGGTGAGCCAGTGTGACCTGCAGCGGCCGCTACT

AGT-3', referring to SEQ ID NO: 73;
``` terminators used by the two fluorescent protein genes 3' are both a terminator rmB T1, and a sequence thereof is:

```
5'-CAAATAAAACGAAAGGCTCAGTCGAAAGACTGGGCCTTTCGTT

Figure 3A:
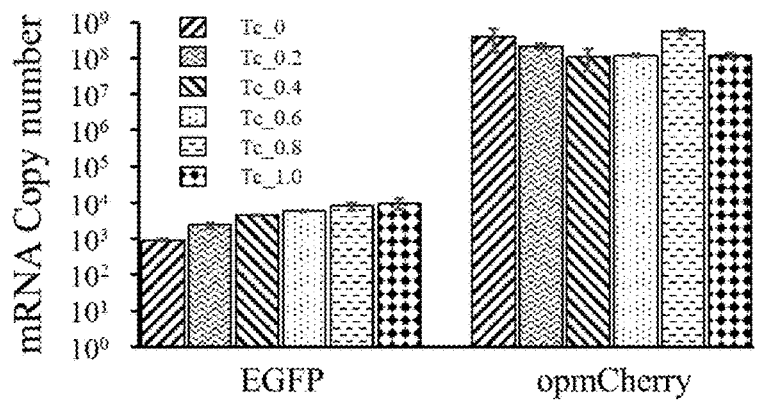
FIG. 3A-FIG. 3F are diagrams of verification results of the dual-fluorescent reporter gene system in different aspects according to the first preferred embodiment of the present invention.
Figure 3B:
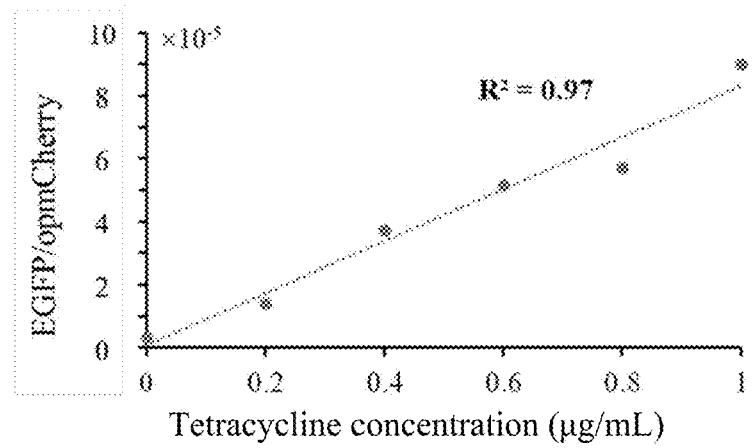
Figure 3C:
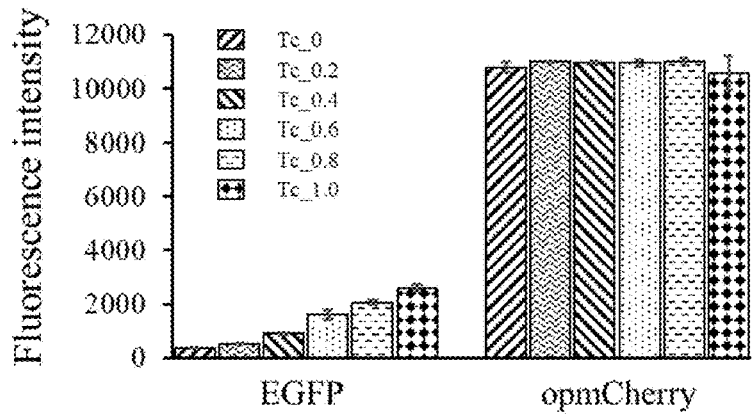
Figure 3D:
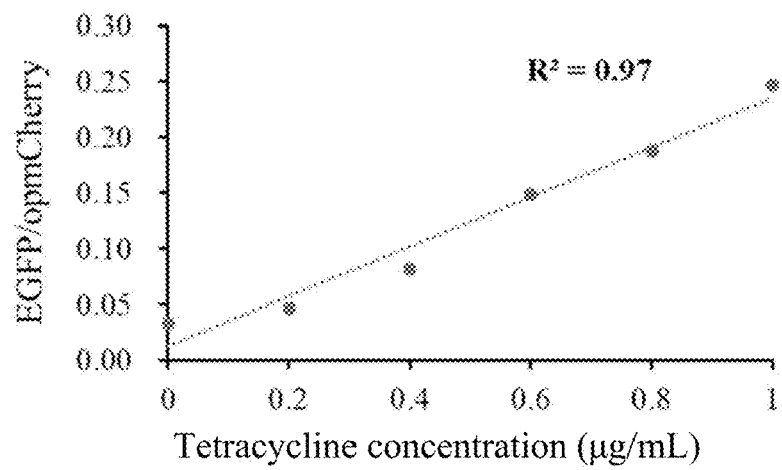
Figure 3E:
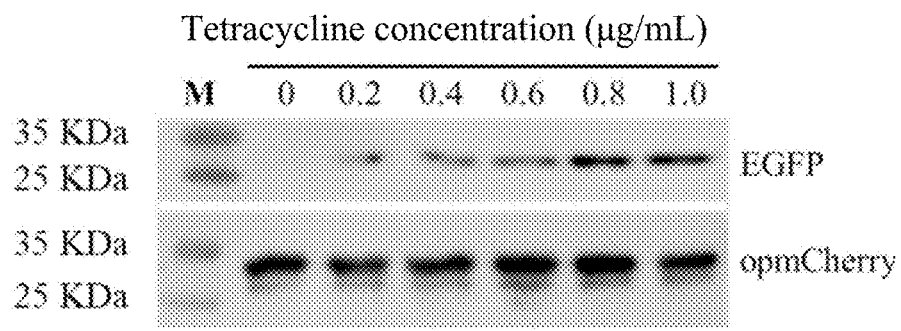
Figure 3F:
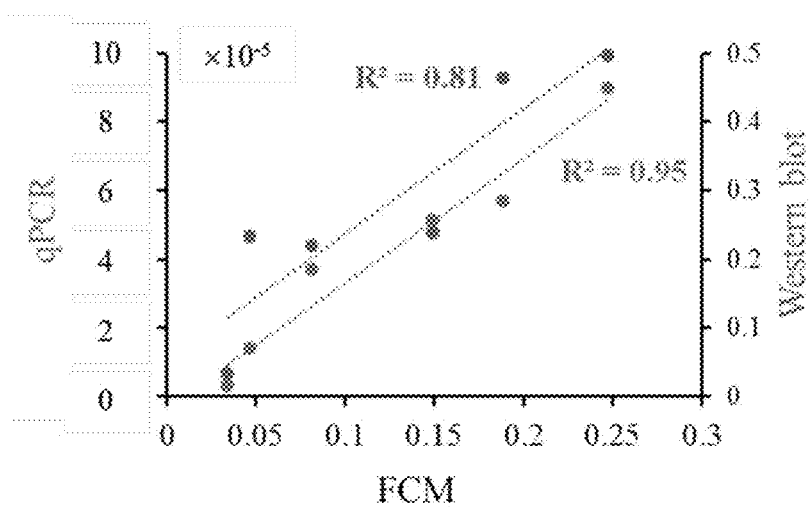

TTA-3', referring to SEQ ID NO: 74;
``` for the modified Gibson assembly method, a system of 5 μL is used in the connection process; a molar ratio of target fragments to vectors is 3:1, 0.5 μL of T5 excision enzyme and 0.5 μL of buffer 4 are added; if the volume is not enough, deionized water is supplemented; the method particularly comprises steps of: after uniformly mixing the system, reacting on ice for 5 minutes; then adding 100 μL of DH5α chemical competent cells; after incubating on ice for 30 minutes, heat-shocking at 42° C. for 45 seconds, and then standing on ice for 2-3 minutes, so that more recombinant vectors will enter the competent cells; after recovering at 37° C. with a rotational speed of 250 rpm for 1 hour, coating to LB (Lysogeny Broth) solid media containing 200 μg/mL of spectinomycin, and culturing in an incubator at 37° C., wherein in other embodiments, antibiotics of other types and concentrations can be selected according to actual requirements; after 12-24 hours, selecting 5-10 single colonies having clear edges for colony PCR, so as to pick out a recombinant; further selecting 2 single colonies having clearest bands, and sending to a sequencing company for sequencing and verifying; after obtaining the sequences, comparing with an original sequence, so as to determine a sequence correctness;

after the sequences are determined to be correct, extracting plasmids with a conventional plasmid miniprep kit, Tsingke; after obtaining the plasmids, electronically transforming the plasmids into the wild-type Z. mobilis; through colony PCR and sequencing, determining a final strain; wherein: sequencing is completed by the Tsingke Company; the obtained sequence is compared with an original sequence, so as to determine a sequence correctness;

the system verification process comprises steps of: after obtaining the strain containing the inducible dual-fluorescent reporter gene system, conducting inducing culture with tetracycline having a concentration of 0, 0.2 μg/mL, 0.4 μg/mL, 0.6 μg/mL, 0.8 μg/mL or 1.0 μg/mL, wherein a sampling time is the logarithmic phase; and verifying the dual-fluorescent reporter gene system in different aspects respectively with FCM (Flow Cytometry), qPCR (quantitative PCR), and WB (Western Blot); wherein: results thereof are shown in FIG. 3A-FIG. 3F; FIG. 3A and FIG. 3B show verification results with qPCR; FIG. 3C and FIG. 3D show verification results with FCM; FIG. 3E shows verification results with WB; and FIG. 3F shows a correlation between qPCR and FCM;

a formula of the RM comprises components of RMG5: 50 g/L glucose, 10 g/L yeast extract, 2 g/L K $H_2PO_4$, and 200 μg/mL spectinomycin; and culture conditions are 30° C. and 100 rpm;

FCM particularly comprises steps of:

(1) activating and culturing mono-clones, which are loaded into the dual-fluorescent reporter gene system and verified to be correct by PCR positive clone verification, in the RM containing the spectinomycin of 200 μg/mL; wherein: in other embodiments, the antibiotics of other types and concentrations can be selected according to actual requirements;

(2) after culturing to the logarithmic phase, taking a sample of 200 μL; centrifuging with a rotational speed of 12000 rpm for 1 minute, so as to remove a supernatant; washing with 1×PBS (Phosphate Buffered Saline) for two times, and re-suspending;

(3) detecting with the flow cytometer, wherein an event start record is 1,000 cells, and detecting is ended until 20,000 cells;

(4) with non-fluorescent strains and strains containing the single fluorescent EGFP and opmCherry as controls, drawing a gate, wherein compensation is made automatically by the software; and (5) for EGFP, adopting an excitation wavelength of 488 nm and a detector of FITC; for opmCherry, adopting an excitation wavelength of 561 nm and a detector of PC5.5; taking average values of three replicate samples and taking the logarithm of log 2, and conducting subsequent data analysis;

qPCR analyzes the transcriptional levels of EGFP and opmCherry in the dual-fluorescent reporter gene system at the same thermal cycling conditions, particularly comprises steps of: with a TRIzol (Invitrogen, USA) method, extracting the total RNA of the logarithmic-phase sample, and detecting the quality of the extracted RNA with NanoDrop 800; then, according to operation instructions of the commercial kit iScript™ gDNA Clear cDNA Synthesis Kits (Bio-Rad, USA), removing the genome DNA and inversely transcribing into cDNA; conducting the qPCR fluorescent quantitative reaction on the instrument CFX96 Real-Time System (Bio-Rad, USA) with the kit iTaq™ Universal SYBR® Green Supermix (Bio-Rad, USA); wherein: the primers used in the experiment are high-purity salt-free primers having an annealing temperature of 60° C.; sequences of the primers are listed as follows:

| Name | Sequence |
|---|---|
| Q-EGFP-F | TATATCACCGCCGACAAGCA |
| Q-EGFP-R | CGCTTCTCGTTGGGGTCTTT |
| Q-CH-F | CACCAATTTCCCGAGCGATG |
| Q-CH-R | AAACGCTGCTTGATTTCGCC | after analyzing the specificity of the PCR product through the melting curve, detecting according to a following program, particularly comprising steps of: denaturing at 95° C. for 5 minutes; completing 40 amplification cycles (95° C. 15 s, 60° C. 10 s, and 72° C. 30 s); quantitatively detecting the single fluorescent proteins; with the absolute quantitative method based on the internal-reference calibration curve, conducting the qPCR data analysis;

Western Blot particularly comprises steps of:

using the protein extraction kit (Zomanbio, China) for cell lysis and total protein extraction; with the Bradford method, quantifying the protein loading quantity to 200 ng; conducting SDS-PAGE (Sodium Dodecyl Sulfate-Polyacrylamide Gel Electrophoresis) with 5% stacking gel and 12% separating gel; with the pre-stained protein Marker (10-170 kDa, Thermo, Lithuania), distinguishing the size of the protein bands; after completing electrophoresis, with the Trans-Blot® Semi-Dry Electrophoretic Transfer Cell (Bio-Rad, USA) system, transferring the target protein (EGFP or opmCherry) to the PVDF (Polyvinylidene Fluoride) membrane immersed in methyl alcohol, wherein transferring conditions are 25 V and 20 minutes; after membrane transferring, sealing at a room temperature for 1 hour with 5% skim milk powders; after completing sealing, incubating the primary antibodies (Proteintech, China) of EGFP or opmCherry with a ratio of 1:5000; after incubating at the room temperature for 1 hour, washing with 1×PBST every 5 minutes, totally washing for three times; then, incubating the secondary antibodies (Peroxidase-conjugated goat anti-Mouse IgG) of EGFP or opmCherry also with a ratio of 1:5000; after incubating at the room temperature for 1 hour, washing with 1×PBST every 5 minutes, totally washing for three times; preparing the gel substrate (Immobilon Western Chemiluminescent HRP Substrate) with a ratio of 1:1; and imaging with AI600 Imaging System (GE, USA);

the results are shown in FIG. 3A-FIG. 3F; qPCR, WB and FCM are used for detecting the expressions of the two fluorescent proteins in the transcription and translation levels under different tetracycline concentrations; in order to eliminate the influences from the internal and external environments of the cells, the ratio of EGFP/opmCherry is used for representing the intensities of the promoters to be detected and other biological parts; the experimental results indicate that the expressions of opmCherry in the different levels are all relatively stable, while the expression of EGFP increases with the increase of the tetracycline concentration; the ratio of EGFP/opmCherry is linearly positively related to the tetracycline concentration; moreover, the FMC is also linearly positively related to qPCR and WB, implying the feasibility of quantitatively identifying the potential genetic parts with the high-throughput FMC;

(S5) with the dual-fluorescent reporter gene system as a template, conducting PCR amplification with a primer Prtt-F and a primer Prtt-R, and obtaining a dual-fluorescent reporter gene system skeleton; wherein:

preparation of a PCR system is:

| Reagent | Volume | Concentration |
| --- | --- | --- |
| Prtt-FZR | 2 μL | 10 μM |
| primerSTAR | 25 μL | 2× |
| template | 1 μL | 1 ng |
| ddH$_2$O | Up to 50 μL | | setting of a PCR program is: pre-denaturing at 98° C. for 3 minutes, denaturing at 98° C. for 10 seconds, annealing at 55° C. for 10 seconds, and extending at 72° C. for 50 seconds, totally 29 cycles;

```
a sequence of the primer
Prtt-F is
5'-ATGGTGAGCNAGGGCGAG-3',
referring to SEQ ID NO: 3;

a sequence of the primer
Prtt-R is
5'-ACTAGTAGCGGCCGCTG-3',
referring to SEQ ID NO: 4;
```

(S6) through the modified Gibson assembly method, transforming the biological parts to be detected and the dual-fluorescent reporter gene system skeleton obtained in the step of S5 into *Escherichia coli* DH5α; wherein:

for the modified Gibson assembly method, a system of 5 μL is used in the connection process; a molar ratio of target fragments to vectors is 3:1, 0.5 μL of T5 excision enzyme and 0.5 μL of buffer 4 are added; if the volume is not enough, deionized water is supplemented; the method particularly comprises steps of: after uniformly mixing the system, reacting on ice for 5 minutes; then adding 100 μL of DH5α chemical competent cells; after incubating on ice for 30 minutes, heat-shocking at 42° C. for 45 seconds, and then standing on ice for 2-3 minutes, so that more recombinant vectors will enter the competent cells; after recovering at 37° C. with a rotational speed of 250 rpm for 1 hour, coating to LB solid media containing 200 μg/mL of spectinomycin, and culturing in an incubator at 37° C., wherein in other embodiments, antibiotics of other types and concentrations can be selected according to actual requirements; after 12-24 hours, selecting 5-10 single colonies having clear edges for colony PCR, so as to pick out a recombinant; further selecting 2 single colonies having clearest bands, and sending to a sequencing company for sequencing and verifying; after obtaining the sequences, comparing with an original sequence, so as to determine a sequence correctness; wherein:

preparation of a colony PCR system is:

| Reagent | Volume | Concentration |
| --- | --- | --- |
| Pseq-F/R | 0.2 μL | 10 μM |
| T5 Mix | 5 μL | 2× |
| template | 0.5 μL | single colony aqueous solution |
| ddH$_2$O | Up to 10 μL | | setting of a colony PCR program is: pre-denaturing at 98° C. for 3 minutes, denaturing at 98° C. for 10 seconds, annealing at 55° C. for 10 seconds, and extending at 72° C. for 30 seconds, totally 25 cycles;

```
a sequence of the primer Pseq-F is
5'-GCCATTGACGCTACCTT-3';

a sequence of the primer Pseq-R is
5'-TGGTGGCATCGCCCTCG-3';
``` after the sequences are determined to be correct, extracting plasmids with the conventional plasmid miniprep kit, Tsingke; after obtaining the plasmids, electronically transforming the plasmids into the wild-type *Z. mobilis*; through colony PCR and sequencing, determining a final strain; wherein: sequencing is completed by the Tsingke Company; the obtained sequence is compared with an original sequence, so as to determine a sequence correctness;

(S7) transforming the recombinant plasmids extracted in the step of S6 into ZM4 competent cells; activating and culturing to a logarithmic phase, then detecting and verifying with the flow cytometer.

Figure 5:
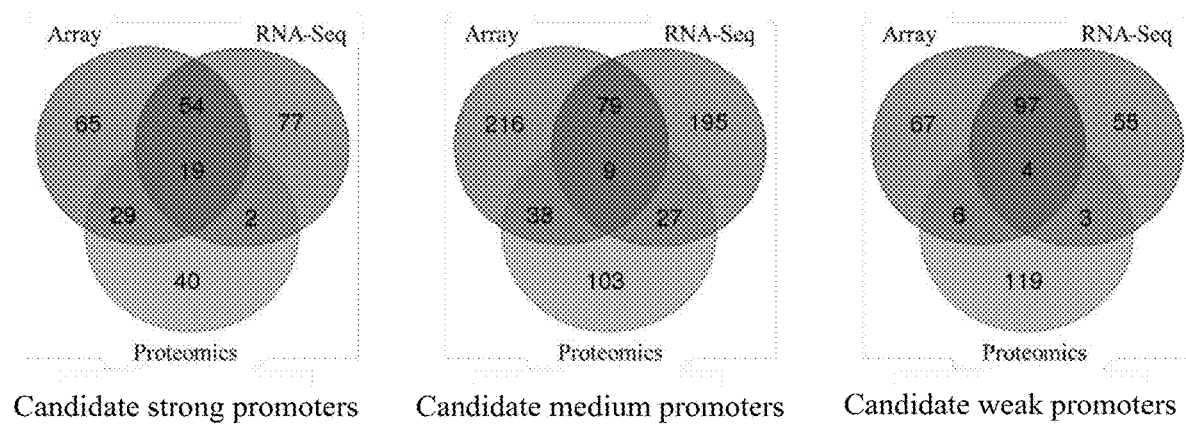
FIG. 5 is a sketch view of screening the promoters of different intensities with Venn analysis according to the second preferred embodiment.

Second Preferred Embodiment: Method for Obtaining Endogenous Promoters of Different Intensities and Method for Identifying Endogenous Promoters of Different Intensities The method for screening the endogenous promoters comprises steps of: according to different omics data, screening out genes having strong downstream expressions, and conducting Venn analysis, as shown in FIG. 5; and then screening out shared genes of each omics data. In the different omics data, the genes are sequenced according to an average value of each gene under all conditions, wherein: the genes ranked above 90% are defined as strong promoters; the genes ranked between 40%-60% are defined as medium promoters; and the genes ranked below 10% are defined as weak promoters. 19 strong promoters, 9 medium promoters, and 10 weak promoters are screened out, and details are listed in Table 1.

TABLE 1

Endogenous promoter genes of different intensities of Z. mobilis and corresponding system biological data and FACS (Fluorescence Activated Cell Sorting) verification results according to second preferred embodiment

| Gene ID | Gene name | Whether is operon? | Gene array | Transcriptomics | Proteomics | Verification results |
|---|---|---|---|---|---|---|
| Strong promoter | | | | | | |
| ZMO0177 | gap | | 15.06 | 11.20 | 9.23 | 0.38 |
| ZMO1360 | pdc | | 14.52 | 11.78 | 8.59 | 0.24 |
| ZMO0516 | Tuf | ND | 15.33 | 11.58 | 8.08 | 0.24 |
| ZMO1608 | eno | | 15.22 | 13.20 | 8.97 | 0.23 |
| ZMO0997 | eda | Yes | 14.97 | 14.60 | 8.46 | 0.18 |
| ZMO0367 | zwf | | 14.92 | 11.19 | 7.38 | 0.16 |
| ZMO1719 | frk | | 15.06 | 12.20 | 6.85 | 0.12 |
| ZMO1609 | | | 15.26 | 12.77 | 5.78 | 0.12 |
| ZMO0689 | gfo | | 14.49 | 11.68 | 6.38 | 0.10 |
| ZMO1721 | gloA3 | ND | 14.35 | 12.66 | 5.97 | 0.09 |
| ZMO0514 | rpsG | Yes | 15.31 | 10.79 | 5.54 | 0.07 |
| ZMO0515 | | Yes | 15.07 | 11.14 | 5.83 | 0.07 |
| ZMO1596 | adhB | | 15.32 | 10.98 | 7.07 | 0.07 |
| ZMO1141 | ilvC | Yes | 15.41 | 12.39 | 6.76 | 0.05 |
| ZMO0241 | atpD | Yes | 15.09 | 11.73 | 7.77 | 0.05 |
| ZMO0244 | | | 14.79 | 12.98 | 6.10 | 0.04 |
| Po1721 | | | | | | 0.04 |
| ZMO0493 | glnA | Yes | 14.53 | 10.02 | 6.17 | 0.03 |
| ZMO1779 | | Yes | 15.08 | 11.24 | 7.52 | 0.02 |
| Medium Promoter | | | | | | |
| ZMO1351 | clcD1 | Yes | 12.93 | 6.81 | 3.14 | 0.14 |
| ZMO0056 | glmS | | 12.93 | 6.91 | 2.45 | 0.12 |
| ZMO0559 | | | 12.68 | 6.75 | 3.10 | 0.11 |
| ZMO1385 | | | 12.83 | 6.93 | 2.55 | 0.06 |
| ZMO0127 | | Yes | 12.84 | 7.11 | 3.13 | 0.05 |
| ZMO1100 | | Yes | 12.58 | 7.18 | 2.82 | 0.05 |
| ZMO1392 | | | 12.46 | 7.43 | 2.45 | 0.04 |
| ZMO0326 | | | 12.65 | 7.41 | 2.70 | 0.03 |
| ZMO0570 | prmA | | 12.38 | 7.32 | 2.45 | 0.03 |
| Weak promoter | | | | | | |
| ZMO1231 | recJ | | 11.03 | 5.70 | 0.07 | 0.08 |
| ZMO1980 | gidB | Yes | 10.59 | 5.27 | 0.07 | 0.05 |
| ZMO1484 | | | 10.93 | 5.40 | 0.07 | 0.05 |
| ZMO0145 | | Yes | 11.37 | 4.98 | 0.07 | 0.04 |
| ZMO0101 | | | 10.61 | 5.05 | 0.07 | 0.04 |
| ZMO1194 | dprA | Yes | 10.70 | 4.77 | 0.07 | 0.04 |
| ZMO1644 | | | 10.61 | 4.98 | 0.07 | 0.03 |
| ZMO1582 | | | 10.33 | 4.63 | 0.07 | 0.03 |
| ZMO0005 | cysD | Yes | 11.50 | 5.28 | 0.07 | 0.03 |
| ZMO0300 | xseA | | 11.60 | 4.71 | 0.07 | 0.03 |

The method for identifying the endogenous promoters comprises steps of operating according to steps of S1-S6 in the first preferred embodiment, wherein: in the step of S6, the endogenous promoters Pgap of certain intensity are experimented, as the biological parts to be detected; in other embodiments, the promoters of other intensities, the promoters containing the RBS (Ribosome Binding Site) sequences of different intensities, or other biological parts can be selected for being detected.

A sequence of the promoter Pgap is:
5'-GTTCGATCAACAACCCGAATCCTATCGTAATGATGTTTTGCCCGATC

AGCCTCAATCGACAATTTTACGCGTTTCGATCGAAGGAGGGACGACAATT

GGCTCTGCTAACGGTATACTGGAKrAAATGCTTCTTCGTTATCTGTATTG

ATGTTTTTGGTGCATCGGCCCCGGCGAATGATCTATATGCTCATTTCGGC

TTGACCGCAGTCGGCATCACGAACAAGETTGTTGGccGCGATCGCCGGTA

-continued

AGTCGGCACGTTAAAAAATAGCTATGGAATATAGTAGCTACTTAATAAGT

TAGGAGAATAAAC-3', referring to SEQ ID NO: 5.

The promoter Pgap is obtained through steps of: with Z. mobilis ZM4 as a template, conducting PCR amplification with a primer P0177-F and a primer P0177-R, and obtaining promoter fragments, wherein lowercases at a 5' terminal of each primer are homologous arms of the dual-fluorescent reporter gene system; according to a PCR recovery kit, recovering and purifying a PCR product; wherein:

preparation of a PCR system is:

| Reagent | Volume | Concentration |
|---|---|---|
| P0177-F/R | 2 μL | 10 μM |
| primerSTAR | 25 μL | 2× |
| template | 1 μL | 1 ng |
| ddH$_2$O | Up to 50 μL | | setting of a PCR program is: pre-denaturing at 98° C. for 3 minutes, denaturing at 98° C. for 10 seconds, annealing at 55° C. for 10 seconds, and extending at 72° C. for 10 seconds, totally 29 cycles;

```
a sequence of the primer P0177-F is
5'-gcggccgctactagtGTTCGATCAACAACCCGAATC-3',
referring to SEQ ID NO: 6;

a sequence of the primer P0177-R is
5'-gcccttgctcaccatGTTTATTCTCCTAACTTATTAAGTAGC-3',
referring to SEQ ID NO: 7.
```

The method further comprises a step of: (S7) transforming the recombinant plasmids extracted in the step of S6 into ZM4 competent cells; activating and culturing to a logarithmic phase, then detecting and verifying with a flow cytometer.

According to the second preferred embodiment, the recombinant plasmids are electronically transformed into the ZM4 competent cells, particularly comprising steps of: placing the ZM4 competent cells on ice; after the ZM4 competent cells melt, taking 50 μL of the competent cells and adding into an electro-transformation cup, and then adding 1 μg of the plasmids into the electro-transformation cup, wherein electro-transformation conditions are 1600 V, 25 μF and 200Ω; after completing electro-transformation, resuscitating at 30° C. in RM; centrifuging a culture, which is obtained after 6-12 hours of resuscitation, with a rotational speed of 6000 rpm for 1 minute, so as to remove a supernatant; adding 200 μL of fresh RM; taking a sample of 100 μL and coating on a resistant plate containing spectinomycin of 200 μg/mL (in other embodiments, antibiotics of other types and concentrations can be selected according to actual requirements); culturing at 30° C. for 2 days; and, conducting PCR positive clone verification with a primer Pdual-F and a primer Pdual-R, wherein:

preparation of a colony PCR system is:

| Reagent | Volume | Concentration |
|---|---|---|
| Pdual-F/R | 0.2 μL | 10 μM |
| T5 c | 5 μL | 2× |
| template | 0.5 μL | single colony aqueous solution |
| ddH$_2$O | Up to 10 μL | | setting of a colony PCR program is: pre-denaturing at 98° C. for 3 minutes, denaturing at 98° C. for 10 seconds, annealing at 55° C. for 10 seconds, and extending at 72° C. for 30 seconds, totally 25 cycles;

```
a sequence of the primer
Pdual-F is
CCGCTCACAATTCCACACATTATAC,
referring to SEQ ID NO: 8;
and a sequence of the primer
Pdual-R is
ACCAGGATGGGCACCAC,
referring to SEQ ID NO: 9.
```

The detecting process with FCM comprises steps of: activating 38 mono-clones, which are verified to be correct, in the RM containing the spectinomycin of 200 μg/mL (in other embodiments, antibiotics of other types and concentrations can be selected according to actual requirements); after activating, culturing three parallels for each sample; after culturing to the logarithmic phase, taking a sample of 200 μL; centrifuging with a rotational speed of 12000 rpm for 1 minute, so as to remove a supernatant; washing with 1×PBS for two times, and re-suspending; detecting with the flow cytometer according to a set program, wherein a cell collection event is set to be 20,000 in the second preferred embodiment, so as to avoid small-probability and accidental events.

Result analysis: according to data obtained by the flow cytometer, for each sample, calculating with average fluorescent values of EGFP and opmCherry of all the events; and standardizing with a ratio of EGFP/opmCherry, so as to eliminate interferences from the internal and external of the cells. The results thereof are shown in FIG. 4A and FIG. 4B.

Figure 4A:
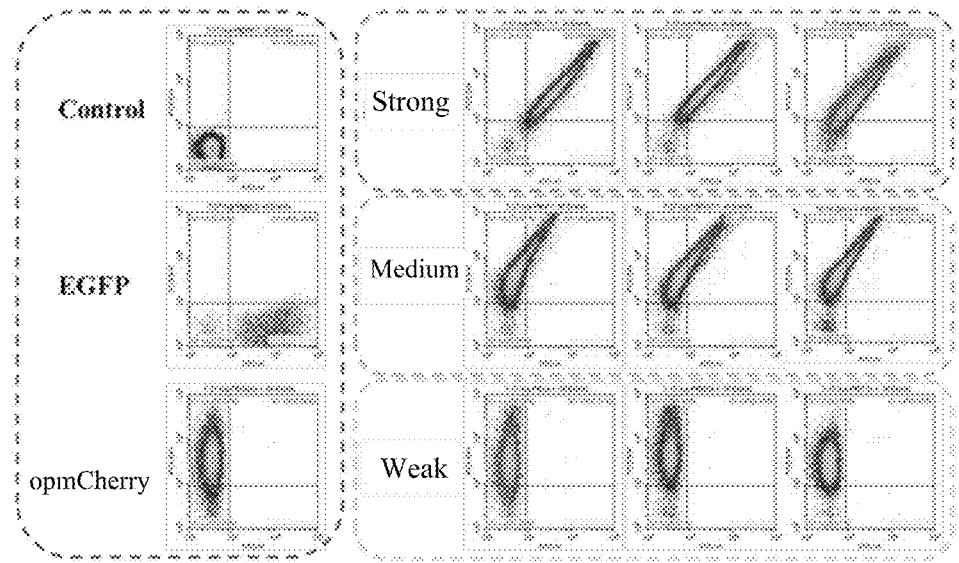
FIG. 4A shows flow cytometer modes of promoters of different intensities according to a second preferred embodiment of the present invention.
Figure 4B:
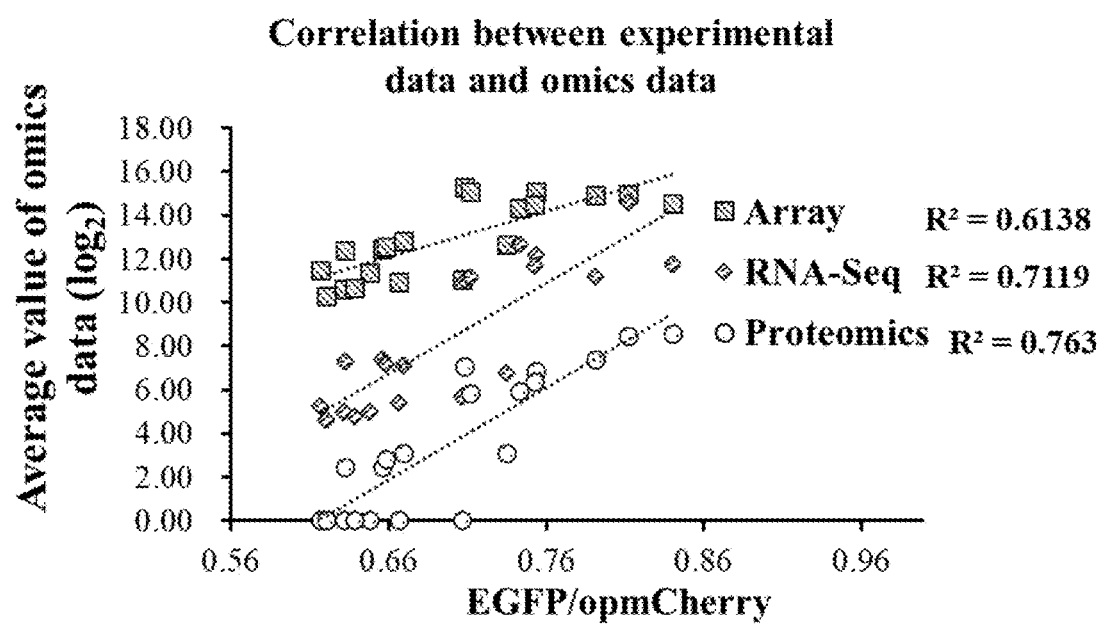
FIG. 4B shows a correlation between experimental data and omics data according to the second preferred embodiment of the present invention.

FIG. 4A shows flow cytometer modes of promoters of different intensities; and FIG. 4B shows a correlation between experimental data and omics data.

The results indicate that: the biological part promoters loaded in the dual-fluorescent reporter gene system can be quickly and quantitatively analyzed with the flow cytometer; the ratio of EGFP/opmCherry represents the relative intensity of the tested promoters in the system; the correlation between the experimental results and the intensities predicted by the omics data is relatively high, illustrating that the dual-fluorescent reporter gene system can be applied in identifying the intensities of the promoters.

Third Preferred Embodiment: Method for Obtaining Promoters Containing Synthetic RBS Sequences of Different Intensities The method comprises steps of:

(Sa) according to different omics data, screening out genes having strong downstream expressions; then conducting Venn analysis; and screening out shared genes of each omics data;

(Sb) predicting the RBS sequences of different intensities with RBS Calculator V2.0 according to 16s rRNA of Z. mobilis; wherein:

```
referring to SEQ ID NO: 10, a sequence of
Z. mobilis 16S rRNA is:
5'-AACTTGAGTTTGATTCTGGCTCAGAACGAACGCTGGCGGCATGCTTA

ACACATGCAAGTCGAACGAAGGCTTCGGCCTTAGTGGCGCACGGGTGCGT

AACGCGTGGGAATCTGCCTTCAGGTACGGAATAACTAGGGGAAAOVGAGC

TAATACCGTATGACATCGAGAGATCAAAGATTTATCGCCTGAAGATGAGC

CCGCGTTGGATTAGCTAGTTGGTAGGGTAAAAGCTTACCAAGGCGACGAT

CCATAGCTGGTCTGAGAGGATGATCAGCCACACTGGGACTGAGACACGGC

CCAGACTCCTACGGGAGGCAGCAGTGGGGAATATTGGACAATGGGGGAAA

CCCTGATCCAGCAATGCCGCGTGAGTGAAGAAGGCGTAGGGTTGTAAAGC

TCTTTTACCCGGGATGATAATGACAGTACCGGGAGAATAAGCTCCGGCTA

ACTCCGTGCCAGCAGCCGCGGTAATACGGAGGGAGCTAGCGTTGTTCGGA

ATTACTGGGCGTAAAGCGTACGTAGGCGGTTTAATAAGTCAGGGGTGAAA

GCCCAGAGCTTCAACTCTGGAACTGCCTTTGAGACTGTTAGACTAGAACA

TAGAAGAGGTAAGTGGAATTCCGAGTGTAGAGGTGAAATTCGTAGATATT

CGGAAGAACACCAGTGGCGAAGGCGACTTACTGUTCTATAGTTGACGCTG

AGGTACGAAAGCGTGGGTTAGCAAACAGGATTAGATACCCTGGTAGTCCA
```

-continued
CGCCGTAAACGATGATAACTAGCTGTCCGGGTACATGGTATGGGTGGCGG

AGCTAACGCATTAAGTTATCCGCCTGGGGAGTACGGTCGCAAGATTAAAA

CTCAAAGAAATTGACGGGGGCCTGCACAAGCGGTGGAGCATGTGGTTTAA

TTCGAAGCAACGCGCAGAACCTTACCAGCGTTTGACATCCTGATCGCGGA

AAGTGGAGACACATTCTTTCAGTTCGGCTGGATCAGAGACAGGTGCTGCA

TGGCTGTCGTCAGCTCGTGTCGTGAGATGTTGGGTTAAGTCCCGCAACGA

GCGCAACCCTCACCTCTAGTTGCCATCATTAAGTTGGGCACTTTAGAGGA

ACTGCCGGTGATAAGCCGGAGGAAGGTGGGGATGACGTCAAGTCCTCATG

GCCCTTACGCGCTGGGCTACACACGTGCTACAATGGCGGTGACAGAGGGC

CGCAAGCCTGCAAAGGTTAGCTAATCTCAAAAAGCCGTCTCAGTTCGGAT

TGTTCTCTGCAACTCGAGAGCATGAAGGCGGAATCGCTAGTAATCGCGGA

TCAGCATGCCGCGGTGAATACGTTCCCAGGCCTTGTACACACCGCCCGTC

ACACCATGGGAGTTGGATTCACCCGAAGGCGCTGCGCTAACCCGCAAGGG

AGGCAGGCGACCACGGTGGGTTTAGCGACTGGGGTGAAGTCGTAACAAGG

TAGCCGTAGGGGAACCTGCGGCTGGATCACCTCCTTFCTAAGGA-3';

Table 2 RBS sequences of different intensities of *Z. mobilis* according to third preferred embodiment

| Name | Intensity | Predicted RBS sequence (5'→3') |
|---|---|---|
| ZM4-Ptet-GFP-10 | 10 | CCATAATCTAGAGAAAGTAAGCAC, SEQ ID NO: 11 |
| ZM4-Ptet-GFP-1000 | 1000 | AGGCTAAGAACTAACGGAGAGGTAAAT, SEQ ID NO: 12 |
| ZM4-Ptet-GFP-10000 | 10000 | ATCACAGGGTCTAGAAGGAGGTCGAA, SEQ ID NO: 13 |
| ZM4-Ptet-GFP-Max | 15000 | GAGCGAGAAGGAGGTAAAGT, SEQ ID NO: 14 |

(Sc) obtaining the promoters containing the RBS sequences of specific intensities, particularly comprising steps of: according to the third preferred embodiment, with RBS-10 as an example and the dual-fluorescent reporter gene system containing the promoter Ptet as a template, conducting PCR amplification with a primer pEZ-tetR-F and a primer RBS-10-R, wherein lowercases at a 5' terminal of each primer are homologous arms of the dual-fluorescent reporter gene system; and obtaining the promoters containing the RBS sequences of specific intensities; wherein:
preparation of a PCR system is:

| Reagent | Volume | Concentration |
|---|---|---|
| pEZ-tetR-F/RBS-10-R | 2 μL | 10 μM |
| primerSTAR | 25 μL | 2× |
| template | 1 μL | 1 ng |
| ddH₂O | Up to 50 μL | | setting of a PCR program is: pre-denaturing at 98° C. for 3 minutes, denaturing at 98° C. for 10 seconds, annealing at 55° C. for 10 seconds, and extending at 72° C. for 20 seconds, totally 29 cycles;

a sequence of the primer pEZ-tetR-F is

5'-gcggccgctactagtTTAAGACCCACTTTGACATTTAAGTTGTTTT TC-3', referring to SEQ ID NO: 15;
and a sequence of the primer RBS-10-R is 5'-gccatgctcaccatGTGCTTACTTTCTCTAGATTATGGAGATCaTT TGAATaCTTTTTCTCTATCACTGATAGGGAGTGG-3', referring to the SEQ ID NO: 16.

After obtaining the promoters containing the RBS sequences of specific intensities, the intensities of the obtained promoters are verified based on the dual-fluorescent reporter gene system, particularly comprising steps of:
with the modified Gibson assembly method, transforming the obtained promoters containing the RBS sequences of specific intensities and the dual-fluorescent reporter gene system skeleton obtained in the first preferred embodiment into *Escherichia coli* DH5α; verifying positive clones on a plate by PCR; after culturing overnight, extracting plasmids, and obtaining recombinant plasmids; wherein: the plasmids are extracted according to standard steps of the plasmid extraction kit;
electronically transforming the extracted recombinant plasmids into the ZM4 competent cells, particularly comprising steps of: placing the ZM4 competent cells on ice; after the ZM4 competent cells melt, taking 50 μL of the competent cells and adding into an electro-transformation cup, and then adding 1 μg of the plasmids into the electro-transformation cup, wherein electro-transformation conditions are 1600 V, 25 μF and 200 S; after completing electro-transformation, resuscitating at 30° C. in RM; centrifuging a culture, which is obtained after 6-12 hours of resuscitation, with a rotational speed of 6000 rpm for 1 minute, so as to remove a supernatant; adding 200 μL of fresh RM; taking a sample of 100 μL and coating on a resistant plate containing spectinomycin of 200 μg/mL (in other embodiments, antibiotics of other types and concentrations can be selected according to actual requirements); culturing at 30° C. for 2 days; and, conducting PCR positive clone verification with a primer Pdual-F and a primer Pdual-R, wherein: sequences of the primer Pdual-F and the primer Pdual-R respectively refer to SEQ ID NO: 8 and SEQ ID NO: 9;
verifying the intensities, particularly comprising steps of: activating mono-clones, which are loaded into the dual-fluorescent reporter gene system and verified to be correct by PCR positive clone verification, in the RM containing the spectinomycin of 200 μg/mL (in other embodiments, antibiotics of other types and concentrations can be selected according to actual requirements); after activating, culturing three parallels for each sample; conducting inducing culture with tetracycline having a concentration of 0, 0.2 µg/mL, 0.4 µg/mL, 0.6 µg/mL, 0.8 µg/mL or 1.0 µg/mL; after culturing to the logarithmic phase, taking a sample of 200 µL; centrifuging with a rotational speed of 12000 rpm for 1 minute, so as to remove a supernatant; washing with 1×PBS for two times, and re-suspending; detecting with the flow cytometer according to a set program, wherein a cell collection event is set to be 20,000 in the third preferred embodiment, so as to avoid small-probability and accidental events.

Figure 6A:
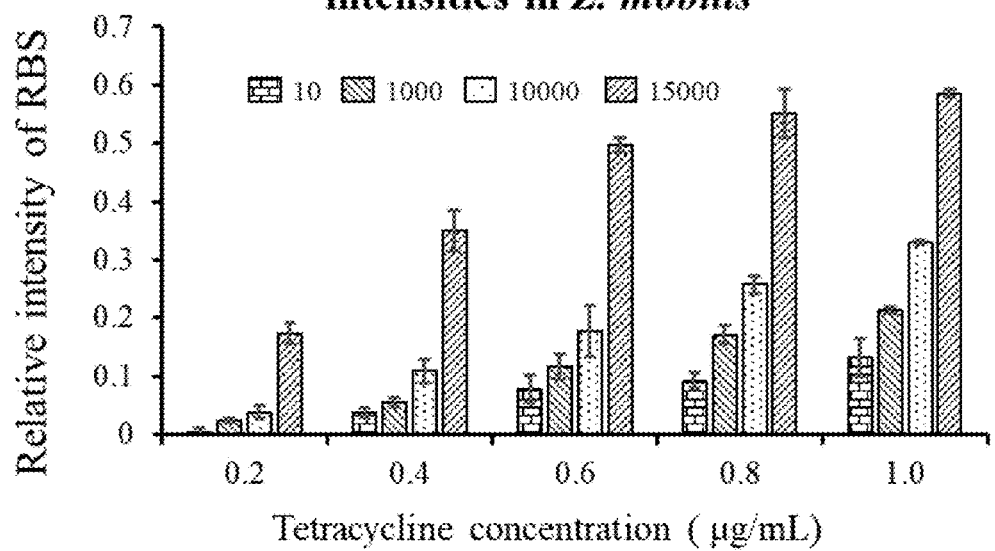
FIG. 6A is a sketch view of intensity verification results of RBS (Ribosome Binding Site) of different intensities according to a third preferred embodiment.
Figure 6B:
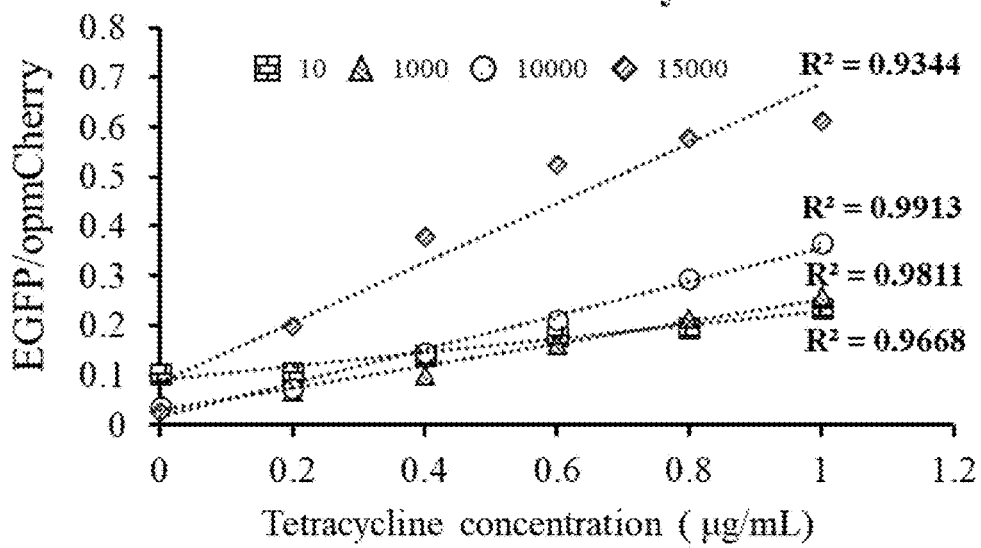
FIG. 6B shows a correlation between the RBS of different intensities and tetracycline concentrations according to the third preferred embodiment.

Result analysis: according to data obtained by the flow cytometer, for each sample, calculating with average fluorescent values of EGFP and opmCherry of all the events; and standardizing with a ratio of EGFP/opmCherry, so as to eliminate interferences from the internal and external of the cells. The results thereof are shown in FIG. 6A and FIG. 6B. FIG. 6A reflects intensity verification of the RBS of different intensities, and FIG. 6B shows a correlation between the RBS intensities and the tetracycline concentrations. The experimental results indicate that: the promoter intensity predicting method based on the omics data according to the third preferred embodiment can be applied in screening the promoters of different intensities.

| | |
|---|---|
| T1929f-F | TGGGAATAACTCAAGCCCCTGCATCGCAGG, referring to SEQ ID NO: 54 |
| T1929f-R | GCCCTTGCTCACCATGCCCCTGCGATGCAGG, referring to SEQ ID NO: 55 |

With the modified Gibson assembly method, the terminator sequence is inserted after the transcriptional start site of the promoter and before EGFP, wherein the used promoter herein is the promoter Pgap.

Through the step of S6 in the first preferred embodiment, the recombinant plasmids are obtained; and then the plasmids are electronically transformed through the step of S7.

Through the step of S7, the intensities care verified.

The terminators only influence the transcription, not influence the translation process. According to the fourth preferred embodiment, the stronger the terminator intensity, the smaller the value of EGFP/opmCherry; the experimental results conform to the predicted intensities Table 3 shows the relevant information of the verified terminators and the verification results with the method provided by the fourth preferred embodiment.

TABLE 3

Relevant information about sequences of terminators of different intensities of Z. mobilis according to fourth preferred embodiment

| Predicted intensity, name and direction | | Upstream gene | Downstream gene | Sequence (Length: bp) | Detecting value |
|---|---|---|---|---|---|
| Strong | T1929f | ZMO1929 | ZMO1930 | gcccctgcatcgcaggggc (referring to SEQ ID NO: 56) | 5.96 |
| Medium | T0671f | ZMO0671 | ZMO0672 | gcgtcgtcgcctttgcgacggcgc (referring to SEQ ID NO: 57) | 8.10 |
| Weak | T0559f | ZMO0559 | ZMO0560 | ggaagggtatagatatatccatatccacc (referring to SEQ ID NO: 58) | 14.05 |
| Strong | T0152r | ZMO0152 | g | gccgggggggacatttctctccggc (referring to SEQ ID NO: 59) | 8.56 |
| Medium | T1145r | ZMO1145 | ZMO1144 | tttcgaggtggcttcggccacctcgtca (referring to SEQ ID NO: 60) | 12.12 |
| Weak | T1155r | ZMO1155 | ZMO1154 | ggtcaacttctctcaaaataggagaagttggcc (referring to SEQ ID NO: 61) | 12.10 |

Fourth Preferred Embodiment: Method for Obtaining Terminators of Different Intensities The method comprises steps of:

(S01) screening a gene set whose contiguous genes in a same transcription direction have large expression differences, and ordering according to the expression differences;

(S02) with a bioinformatics method, predicting terminator sequences between the contiguous genes, and representing the intensities of the terminators by the expression differences between the contiguous genes; and (S03) designing primers for a target terminator sequence, conducting PCR amplification, and obtaining terminator fragments; wherein: in the fourth preferred embodiment, with a terminator T1929f as an example, the PCR amplification is conducted with the primers T1929f-F and T1929f-R and the ZM4 genome as the template, and finally the terminator T1929f fragments are obtained.

Figure 7:
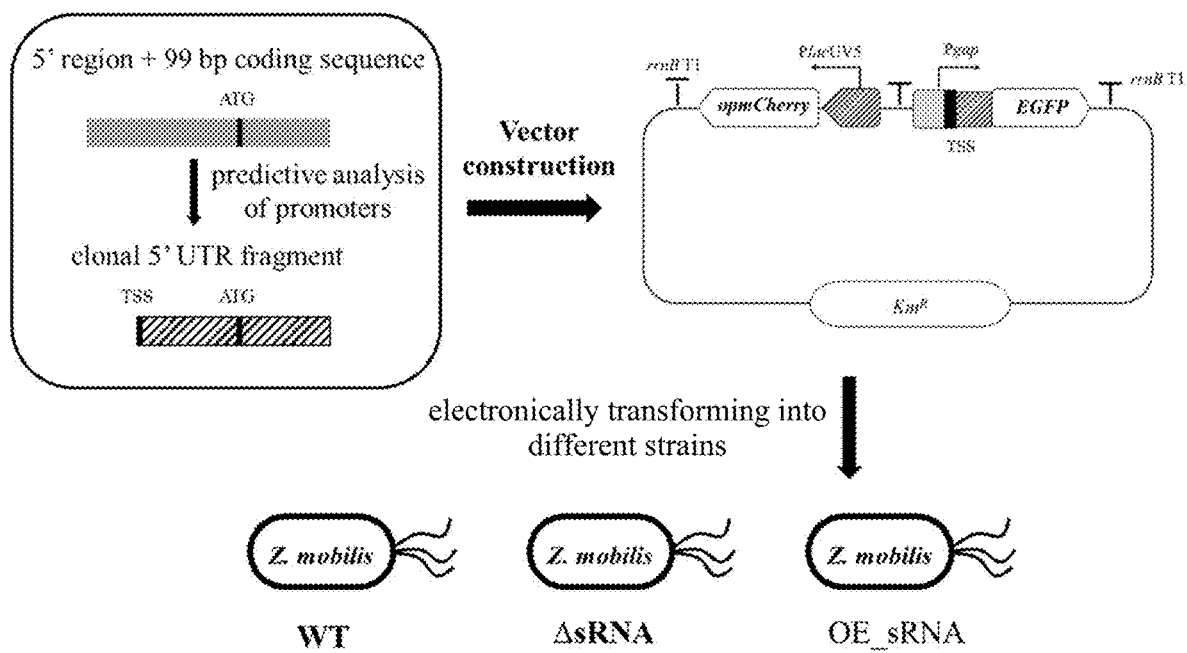
FIG. 7 is a flow chart of a method for identifying interaction of sRNA-UTR according to a fifth preferred embodiment.

Fifth Preferred Embodiment: Method for Identifying Interactive Relationships of sRNA-UTR Interaction Pairs The method comprises steps of:

(S0a) with a bioinformatics method, analyzing a target sequence; after determining a transcriptional start site, retaining the sequence from the transcriptional start site to 99-bp after an initiation codon ATG, as a target 5' UTR sequence; wherein:

verification of the interaction between sRNA Zms4 and the gene ZMO1754 UTR (Zms4-UTR1754) is described in detail as an example, and experimental principles thereof are shown in FIG. 7, particularly comprising steps of:

taking the intermediate sequence between the gene ZMO1754 and the previous gene; conducting promoter analysis with a BPROM program; after obtaining the TSS (Transcriptional Start Site), retaining the sequence from the TSS to 99-bp after the initiation codon ATG of the gene ZMO1754 as the UTR1754 sequence, referring to SEQ ID NO: 62;

the UTR1754 sequence is:
5'-GATCATTTCACAAAAAATGAGAAAAAATTAAGGATGAGTCCTTCTTT
GTAAAAAGGAGGACTGTCCTAAGCTGAAGTAATAAGAAAGGTAGGCTCTT
TTATGGCATATGAATCTGTCAATCCCGCCACTGGCGAAACCGTCAAAAAA
TATCCTGATTTTTCTGATAAACAGGTTAAAGATTCCGTTGATCGGGCGGC
G-3';

(S0b) with a Z. mobilis genome as a template, designing a forward primer and a reverse primer, conducting PCR amplification, and obtaining the target UTR sequence fragments; the step of S0b particularly comprising steps of:

with the Z. mobilis genome as the template, conducting PCR amplification with the primer UTR1754-F and the primer UTR1754-R, and obtaining the UTR1754 sequence; according to a PCR recovery kit, recovering and purifying a PCR product (the lowercases in the sequence of each primer are the homologous arms, and the uppercases are the primer sequences); wherein:

preparation of a PCR system is:

| Reagent | Volume | Concentration |
|---|---|---|
| UTR1754-F/R | 2 μL | 10 μM |
| primerSTAR | 25 μL | 2× |
| template | 1 μL | 1 ng |
| ddH$_2$O | Up to 50 μL | | setting of a PCR program is: pre-denaturing at 98° C. for 3 minutes, denaturing at 98° C. for 10 seconds, annealing at 55° C. for 10 seconds, and extending at 72° C. for 10 seconds, totally 29 cycles;

a sequence of the primer UTR1754-F is:
5'-atggtattgatgtttGATCATTTCACAAAAAATGAGAAAAAATTAAG
GATGAG-3', referring to SEQ ID NO: 63;

a sequence of the primer UTR1754-R is:
5'-gcccttgctcaccatCGCCGCCCGATCAACG-3',
referring to SEQ ID NO: 64;

(S0c) with the dual-fluorescent reporter gene system containing the promoter Pgap as the template, conducting PCR amplification with a primer Prtt-F and a primer PgapTSS-R, and obtaining the dual-fluorescent reporter gene system skeleton; according to the PCR recovery kit, recovering and purifying the PCR product; wherein:

in the first preferred embodiment, when verifying the intensity of the promoter Pgap, the dual-fluorescent reporter gene system containing the promoter Pgap has been obtained, and thus it is used as the template in the fifth preferred embodiment;

a sequence of the primer Prtt-F is
5'-ATGGTGAGCAAGGGCGAG-3',
referring to SEQ ID NO: 3;

a sequence of the primer PgapTSS-R is
5'-AAACATCAATACCATAACGAAGACC-3',
referring to SEQ ID NO: 65;

(S0d) obtaining recombinant plasmids, particularly comprising steps of: after obtaining the UTR sequence and the dual-fluorescent reporter gene system skeleton, with the modified Gibson assembly method, transforming into Escherichia coli DH5α; verifying positive clones on a plate by PCR; after culturing overnight, extracting plasmids (the plasmids are extracted according to standard steps of the plasmid extraction kit);

(S0e) obtaining the strains of the dual-fluorescent reporter gene system plasmids, which contain the specific UTR sequences, particularly comprising steps of: electronically transforming the Z. mobilis wild-type strains, Zms4 knock-out strains and over-expressed strains with the extracted plasmids; placing the corresponding competent cells on ice; after the competent cells melt, taking 50 μL of the competent cells and adding into an electro-transformation cup, and then adding 1 μg of the plasmids into the electro-transformation cup, wherein electro-transformation conditions are 1600 V, 25 μF and 200; after completing electro-transformation, resuscitating at 30° C. in RM; centrifuging a culture, which is obtained after 6-12 hours of resuscitation, with a rotational speed of 6000 rpm for 1 minute, so as to remove a supernatant; adding 200 μL of fresh RM; taking a sample of 100 μL and coating on a resistant plate containing kanamycin of 300 μg/mL; culturing at 30° C. for 2 days; and, conducting PCR positive clone verification with a primer Pdual-F and a primer Pdual-R wherein:

a sequence of the Pdual-F is
CCGCTCACAATTCCACACATTATAC, referring to
SEQ ID NO: 8;

a sequence of the Pdual-R is
ACCAGGATGGGCACCAC, referring to
SEQ ID NO: 9;

(S0f) detecting with FCM, particularly comprising steps of: activating mono-clones, which are verified to be correct, in the RM containing the kanamycin of 300 μg/mL; after activating, culturing three parallels for each sample; after culturing to the logarithmic phase, taking a sample of 200 μg; centrifuging with a rotational speed of 12000 rpm for 1 minute, so as to remove a supernatant; washing with 1×PBS for two times, and re-suspending; detecting with the flow cytometer according to a set program, wherein a cell collection event is set to be 20,000, so as to avoid small-probability and accidental events.

Result analysis: according to data obtained by the flow cytometer, for each sample, calculating with average fluorescent values of EGFP and opmCherry of all the events; and standardizing with a ratio of EGFP/opmCherry, so as to eliminate interferences from the internal and external of the cells. The results thereof are shown in FIG. 8A and FIG. 8B.

In a similar way, the interactive relationship of Zms4-UTR1993 is identified.

Figure 8A:
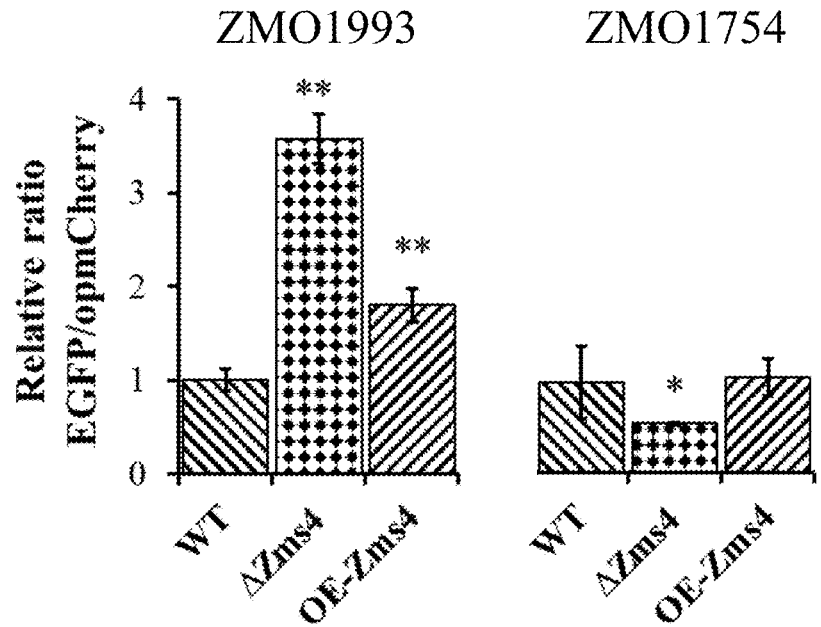
FIG. 8A and FIG. 8B are sketch views of experimental results of interaction between sRNA and target UTR thereof according to the fifth preferred embodiment.
Figure 8B:
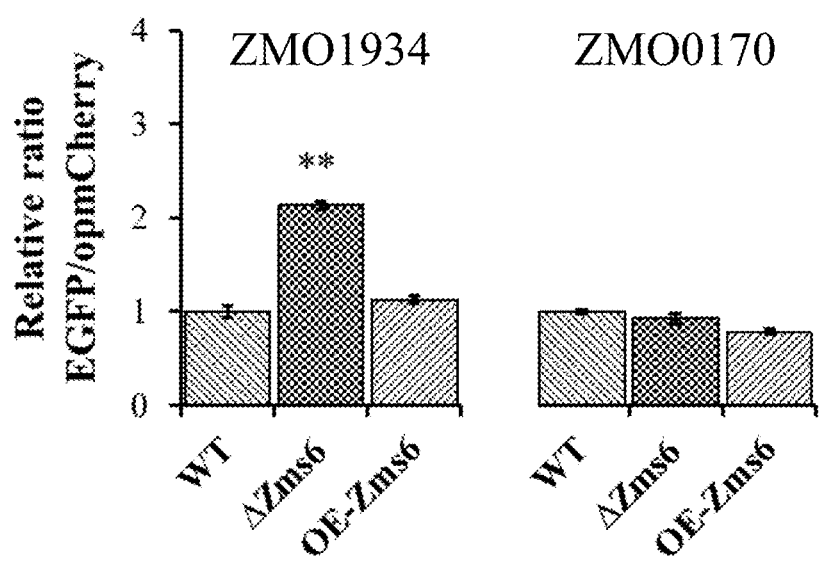

FIG. 8A is a sketch view of the interaction between Zms4 and the target UTR thereof according to the fifth preferred embodiment. The results indicate that: the detecting results of the dual-fluorescent reporter gene system conform to the bioinformatics prediction results. When Zms4 is predicted to have a stabilizing effect on the target UTR (Zms4-UTR1754), the ratio of EGFP/opmCherry in the Zms4 knock-out strains is obviously decreased in comparison with that in the WT strains. When Zms4 is predicted to have a degradation effect on the target UTR (Zms4-UTR1993), the ratio of EGFP/opmCherry in the Zms4 knock-out strains is obviously increased in comparison with that in the WT strains.

The experimental results obtained through the system provided by the present invention is consistent with the results obtained through the conventional experimental method. However, the present invention is quick, convenient, safe and high-efficient, has a short experimental period (save at least one week in comparison with the conventional method), and can conduct batch operation.

Table 4 shows relevant information of the identified interaction pairs with the technical solutions according to the fifth preferred embodiment, wherein: Zms4 nucleotide sequence refers to SEQ ID NO: 66, Zms6 nucleotide sequence refers to SEQ ID NO: 67; UTR1754 nucleotide sequence refers to SEQ ID NO: 68; UTR1993 nucleotide sequence refers to SEQ ID NO: 69; UTR0170 nucleotide sequence refers to SEQ ID NO: 70, UTR1934 nucleotide sequence refers to SEQ ID NO:71, and UTR149 nucleotide sequence refers to SEQ ID NO: 72.

TABLE 4

Identification results of interactive relationships of sRNA-UTR interaction pairs in Z. mobilis according to fifth preferred embodiment

| Interaction pairs | Wild-type strains | sRNA knock-out strains | sRNA over-expressed strains | Predicted Interaction |
| --- | --- | --- | --- | --- |
| Zms4-UTR1754 | 2.51 | 1.37 | 2.64 | Prevents transcript degradation |
| Zms4-UTR1993 | 1.70 | 6.08 | 3.07 | Promotes transcript degradation |
| Zms6-UTR0170 | 0.22 | 0.20 | 0.17 | Promotes transcript degradation |
| Zms6-UTR1934 | 0.75 | 1.61 | 0.85 | Prevents translation |

The sequences of the promoters screened by the step of Sa in the third preferred embodiment are listed as follows.

```
SEQ ID NO: 17
P0177
GTTCGATCAACAACCCGAATCCTATCGTAATGATGTTTTGCCCGATCAGCCTCA
ATCGACAATTTTACGCGTTTCGATCGAAGCAGGGACGACAATTGGCTGGGAACGGTAT
ACTGGAATAAATGGTCTTCGTTATGGTATTGATGTTTTTGGTGCATCGGCCCCGGCGAA
TGATCTATATGCTCATTTCGGCTTGACCGCAGTCGGCATCACGAACAAGGTGTTGGCCG
CGATCGCCGGTAAGTCGGCACGTTAAAAAATAGCTATGGAATATAGTAGCTACTTAAT
AAGTTAGGAGAATAAAC

SEQ ID NO: 18
P1360
AAAGTCACACGGTTCCTTATTTCTTTTCTATCCAAACTCTTTGCAATAGTCTGTA
ACAAGATGACGGCGACGATATCGGATCTTCGTCTCTTTTGGGTCGCGAAAAAATATTAA
CTTTAATCGAAAAAAATTGAGTCTGTTTTTACTCGGGACAAGACCGCCTTTTTTTATCCA
AAGAATATCCCTTTCATCTTCTTTCGAAAGCGAAAAATAAATACTGAAAACAACGGTTT
TGACCACAAGATTCACGGGCTATCCTTCAAAAGAAGAAGCCCTTTTTTATCCTCTCTTA
GGGCGTGGTTAAGGGTTGGCTTGGGCTTAACAAATTTTGTTTATGCACAACTTTGGGTT
GACTTGGCGACAATAAAATATCACCAGAGGGGCAGACCGGTTACGGAAACGTTTCCGC
TTTGATAGCTCAGACGGAGGGAAAGGCTTTGTCAGTGTTGCGGTATAATATCTGTAACA
GCTCATTGATAAAGCCGGTCGCTCGCCTCGGGCAGTTTTGGATTGATCCTGCCCTGTCTT
GTTTGGAATTGATGAGGCCGTTCATGACAACAGCCGGAAAAATTTTAAAACAGGCGTC
TTCGGCTGCTTTAGGTCTCGGCTACGTTTCTACATCTGGTTCTGATTCCCGGTTTACCTTT
TTCAAGGTGTCCCGTTCCTTTTTCCCCTTTTTGGAGGTTGGTTATGTCCTATAATCACTTA
ATCCAGAAACGGGCGTTTAGCTTTGTCCATCATGGTTGTTTATCGCTCATGATCGCGGC
ATGTTCTGATATTTTTCCTCTAAAAAAGATAAAAAGTCTTTTCGCTTCGGCAGAAGAGG
TTCATCATGAACAAAAATTCGGCATTTTTAAAAATGCCTATAGCTAAATCCGGAACGAC
ACTTTAGAGGTTTCTGGGTCATCCTGATTCAGACATAGTGTTTTGAATATATGGAGTAA
GCA

SEQ ID NO: 19
P0516
TTAAATACTGGCATAAACCGAAAAATGTCGTTATGAGCGCGCCGGAGAAGCGC
GGCGCGCTCAATACAATAGTGATAAAAGCGGTAACAAAAAGAGGTAACTA

SEQ ID NO: 20
P1608
TGTCTATACTCCAGTTACTCAATACGTAACAATAATCAGTTTATCCTAACTATA
GAATCGCATGAGAAGCGATAACGTTTCACCATAAGCAATATATTCATTGCAACAGTGG
AATTGCCTTATGCGTCAAGGAAGGATAGATCATTGACGGACTGAGTTCAAAAAGAGAC
TCGTCTAAAAGATTTTAAGAAAGGTTTCGAT

SEQ ID NO: 21
P0997
GGTCGAATGCATTCCTTTCGTTACAGATATATTCCGCTATAAAACTATAGAATA
TAAGTTATGTTCCATTCGCAGAATAGATATAGATCAGCCTCTATGGATATGCTATATAT
CGCCCATTCCATTTAAGAATAATAATAAACCATCATGCTGTTTATTTAATATTTTTATTA
CAGTGAATTGAAGAAATATTTTCTTGATAAAAATTATTAAAAATCTATCACCGACGATC
CGTCTCTATTTCAAGATAGATAATAAATTTGTTTAACCTGTTGATTATGCGAGATAATTTT
A
```

SEQ ID NO: 22
P0367
TTAAACTTGCTTTGGCTGAATCCTTTTGTCTTTTTTAGATAAGTCTTAACCAATT
ATACTTTTTGTTTACAACGATGGTATAAAGCGGGCGGACAGGCTAAAAACAGGCTAAA
AGGATTCGGCCTCTGTTTTAAGGACGAGAATA

SEQ ID NO: 23
P1719
AATCCAAAATATAGAAAAGAAGGTCTGCCTTTTTATTTCGGATACTGTTTTCTG
AATTGTATTTATTACAATTCAGAAAACGAATATTCAAAATCGCAGCATTGCGATAATAA
ATTCCAATTAAATGGCAATAAAGATTGCTAAATTTAGTATCGAAAAGCGTAGAAAACT
ATCGCTTATGCAATAAAAATAAATGTTTCATGACAACGTTGACAAAAAAACTTTTATTT
TTTTCATAAAAAAACACGAATGACACAAAAGAGAATTATTTAAAGACAGAAAAAACAC
AAAAAAAATAACAAATATTACCATTCCTAAAGAAGGACTTCTTTGGACAAAAGAAA
TTTATCTTAGATTCAAGATATCCAAATTATTTTTGAAAAAAATAAAATACATCCAATC
CCGAATTTATTTCGTTTTAAATATCAGCAAAAATATATTTTTTCTTTATTTTTTAAAAA
ATAACTTCATTTTACTTTAAATTTTCCAAGAAAATATTTCGAAAATATTTTTGATATCTT
TCTTAATTAAGAAAGAAAACTTAGTTATAATCCTACCAGTTGGACGAATCGCAGACGGT
CGATTTCGATTTATTCAAAAGGCCTTTTGGCACAGAAGAAAATCGAGGTCATCGTCAT
AATTTAAAGCGAATGGACAGCATATACCTCCGTATTACGGGGGATTTTGTGAGTGGTG
AGAATA

SEQ ID NO: 24
P1609
ATCGAAACCTTTCTTAAAATCTTTTAGACGAGTCTCTTTTTGAACTCAGTCCGT
CAATGATCTATCCTTCCTTGACGCATAAGGCAATTCCACTGTTGCAATGAATATATTGCT
TATGGTGAAACGTTATCGCTTCTCATGCGATTCTATAGTTAGGATAAACTGATTATTGTT
ACGTATTGAGTAACTGGAGTATAGACA

SEQ ID NO: 25
P0689
ACTTTATTATATTGCTCATCTTTGTTAAAAATTATGTATCGATAAAAGATAAAT
ATCATTTATCTTTTATCGATATTTTTTGATTTTGTCTTTGCGTCCAGAAAAGACAGCATT
CCTTCTCAATAAAGAAATATTATTTTTGTTTTTGAAAATTTTTCCAAAATCTAGAATG
CTACATTAAATATACAAAAATATTATTATACAAATAAGGCTTTTAAATACCCATATTTTT
TAGAATTTCTTTACAAAGAAACATGTTAAATATAGATTTAGAGATTAATATCAGCCATT
TTTATCAAAAATTCTTTTTTGTTTTATAATATTATGCTGCAAAACTAATAAAAACGCCC
TTTCGAAATTAACGATCACCCACAAGAAATAATTATCTGACAGCGCTTACCAATCAATT
ATTGCCGAACGCAGAGTCCCGTATTAGGACGGTCAACAATCTAAACCGTTTTTCAGAAA
ATATTGCTTTATAAGCCTCAAAACTTAAAAGCTGCGGTATTTTAATATACCAAAATTTTC
TGGAAAAGCCGGCGAATCAGATAACAGTTCCGCACAGGTGAGAACCACGACGGATCTT
CTCTGAATTGTTGGTTAGTTAAGAAAGAAACAAGGATT

SEQ ID NO: 26
P1721
TCAGTGGTGATCGGTGTTGCCGAGGCTGGAAAAGAAATTTCAACCCGTCCTTT
CCAGTTAGTGACAGGGCGCGTTTGGAAAGGCTCTGCTTTCGGCGGCGTTAAAGGCAGA
ACCGGTGTTCCGAAAATCGTTGACTGGTATATGAAGGGTAAAATTGAAATTGATCCGAT
GATTACCCATATCCTGTCATTAGAAGAGATCAATAAAGCGTTTGACCTGATGCATGAGG
GTAAATCCATTCGTTCGGTTGTTCTTTTCTGATTACCTGTCCTGTTAACCTGTGGATATA
GAAGGTCGGTTTA

SEQ ID NO: 27
P0514
TGGCAGGATAAGTGAAAGAAAATGGGTGTTCACAAAATTGCCCTAGCATGAC
AGAATAAAATTCTTTATATCCTATCGTGGAAACACTGCATGAAAGATCGATTCTGATCA
ATGTAAGGTTTCCATTTCGTAAAATGGCGTAATTTTGTTAGCGGAAAGATGCTTTCCGTT
GACCCTTGCCGTTATCGTCGCTATAGCGCCCGTCTACATCTCCTGTTGACGGTGAATCTT
TGGCGTCAGACGGGTGCGCTTGAACATTGCCATATATGCGCGTCTTCCTTTTAAAGAAT
TCACGCAGGCGAGCTTAGTCATTTTTGCTCGGTGCTATTTTCATAATTTAATTATGGTCA
GGCGCATTTTGTATATTTGGTAAAGTAACTCTTGAGGTGAAGGGCTTC

SEQ ID NO: 28
P1596
AAAAATATATCCCCCCGTTGAATCATTGTTTCCAAAACAGCATCATCTTACTGA
TTTTTGTTTAAAAACAACAAAGATTGTCTCGTCGAGACTGTAAATAGATAAAATATCCG
CTTCCACATAAAAGCGGCAAAAATTTTCAAAATTTCTTTTATTTTTTCATTACCGCTGCA
ATTTTTTTTGTCTTTTTGCGTTTTTTGAGGAAAGCCTGATCTGCCATTTTGAGCAGAAGA
AAGAACAAGCTGCTTTTGATGCAGCGTTTGAGACAATTGATTAGATCAAAAATGGAAA
CGATAATTTTCTTTTTTTTCTATTTTTATTATGGATGAATATCCCTATTTCGGCAGAGCGG
GTGGCGGTAGCACTTCCCCCCCCTCCTCCTCAAGCTACCGCGACCCCCATAGCTTCTTTT
CCTGACTATTCCCCTGCATCCTTACAAATTATTCTTTTATTTCTTTTTCACAATCTATTTG
GATATCTGAAAATGTCTTTATTTTAATGTTGTGCAATTTATACAGTATATTTCGCCATAT
ACGATATTTTCTTGTTTTCTATTTACAATTTGGCTTTTAATATTTGAACAATAAATTGGA
ATGAATACCTAACAACTATGTTATTTTTAGTCTTATCTTTCTCTAAAAAGCCTCAAAAC
GAACAAAATAACAGATTCTTCAAAATTTCCTTTCTTAAAATTTAACATAAATGTTTTATT
TTAAAATATTTCGCCTGAAATTTATTATTTTAATTTAAAGGCAAATCGGTAACCACAT
CTCAATTATTAAACAATACTTCATAATAAAAAGACAACTTTTTCATAATTTGCATAAGT

-continued

CTTGATGTAAAAAATACATATTTAGAAAGAACAAGCAGCCTTGCTCATCACCGCTGTCG
CGAGTAGAAAAATCTCGGCTTTCAGAAAATAGAGGTCGCTTCGTTAAACAGACTATAA
ATGTGCTGGAATAAAGCGAACCCCTTGATCTGATAAAACTGATAGACATATTGCTTTTG
CGCTGCCCGATTGCTGAAAATGCGTAAAATTGGTGATTTTACTCGTTTTCAGGAAAAC
TTTGAGAAAACGTCTCGAAAACGGGATTAAAACGCAAAAACAATAGAAAGCGATTTCT
CGAAAATGGTTGTTTTCGGTTGTTGCTTTAAACTAGTATGTAGGGTGAGGTTATAGCT

SEQ ID NO: 29
P1141
TTGACGTGAATAGTTTTATTCTTTTAAGGCCGTCCTCTACCTTTGCTGTTTTTAA
ATTCACTTAGATTTTTAGCCTTTCCCTTATCAAGGCTACAAACTGAACCATGACAATCAT
CGCGATTGGATCATGGGGTTTCGAAAAGGAAATAAAGC

SEQ ID NO: 30
P0241
TAATTACGCTTTTCAAGGCTGAGACAAAATAACAGCGCTTTCCTTTAGAAAAA
AATGCGCTCTCTTGTTTTTATCGGAAGTTTTTCGGGATTTTCTTGAAAAGTCTCTGATAA
TAGCCACTATTTTGGCAGAAGAGGTCTGAAACCTCTTTTGCCATTTTTGTTTTTTTATGC
TTTATTTTATCGATTTTTTTGAATTTTCGATTTGTGCTAATCGGTTAGCGCCACCTTGCAT
CCCATCCGCCCCCCTGCTAATTAAACTGCGGATCATAACTGGTGAAAATGATTGAAAAG
CCTTCGGGTTTCCATCTTTTATTCTCGCCGGTTTTGTATGCCTATGCGGCATATCCAGTG
TGGCCCTATGTGCGCCCCGGTTGTTTCGAACCGGGACGGAATACAGGGTGAGGCATCTA
TAATCTGGGACGGCAGGCGC

SEQ ID NO: 31
P0244
CACCCAATCCCTTGAAGACTTAAACTTTTAGAAAACAATATGGGGAGATAATA
ATAAATCGCAATCGCTGAGCGCCCAGTTAAGAGAGATTAACAATCTCAAGACACACTC
ATTCCTATGGAGATTCCGCTCTCAATGAAGCGCTAAAAGCAGAATATTTCCTACTTTTCT
TCTCAAAATCATAGAATCAGCCTATCGGCCTATAAATCGAAAAAATGGCTTAAAAATC
ACGCTTTCCGATAAAAACATGAGAAAATTGTTAAATTCGGAGGAAAAATTCATTTTTTC
TTGCAGCATCTGGTGAATAAGCGCTTTGGGCAATATTGCCATTTTTGTCAGGGAATATA
AGAGTCACCAGCTTAAGACGCTGCGATCCCCGCTCGTCTAGTTGCTCAAAGGAAGGAC
AGGATGCCGGAATTAAGATTATAGACAAGGCTCCCATCTTTCTTAATGTAGCGACCACC
GCCGGGATTCATTTCTGACAGGAATGAATCTTAAAAATTTTTCTATTTATTAATGCCATA
GGATCACGAC

SEQ ID NO: 32
Po1721
AGCCTTCAAAGGGCTGGAATATTTTCAGCCCTTACCTCTCTCCAAGGGGATAA
ACGGACAGGCTCCATTATCCCTATTTTATATATCGGGTAACTA

SEQ ID NO: 33
P0493
TGATTATATGAAAAATATTAGAGGACGCAATCTTTTTAATAAAAAATAGGTTA
TATTTTATATAATCCTTGCGAGAAGTTTGGCGTAACTGTAACAACAATACGTTTGAATG
CGCGGGATAGAGGAAGCGCTT

SEQ ID NO: 34
P1779
TGCTGCACCCGTCGTATGATTCCTTTGTCAGGACAACAGGGAAATATTTATCCT
GTTGCTGTCTTGATAAACAGATGAAAAGTGAAAAAGTAATCATCCTCATTGATAAATTT
TTATAATGAGATGTAATTCAATCGCTTTTCCTAGGAAT

SEQ ID NO: 35
P1351
AACTTCTGCTATAACCAATAAGCTTTCCCTTTGCGAGCCGCATTAACATATTCC
GTTTTTGGATTCGGAATATCTGCCGCATCAGAGGAAAGAGGAAAAGGACGGACTGAAA

SEQ ID NO: 36
P0056
AAGACGAAAATATTTCTTACATTGCCCCCATCTCAAAGACAGTCCGCCTTTCAA
AATAGATATCACAAAATCGGGAAACAGAATT

SEQ ID NO: 37
P0559
ATTTTGCGTGCGATCGCTATCCCATGATGAATAGGGATTGCTTCGATATTTTTA
AAAAATTGGGAATAAACTCAA

SEQ ID NO: 38
P1385
AAGCGTTAAATTTCTTTTCGTCTCTTGAAGACCGGAAATAAAAGGCCAGATTTT
ACAGATGGAAGTTGGGGAGTGCCGCTTG

SEQ ID NO: 39
P0127
ATTCAATCAAGTATTATTTCAACAAGGGGAAAGATTGCTTGCTGTAATTTTTGG
ATATCAAACAGGCGAAAAAATGAAAGAGCGCAGCCTCTTTCAAAGGCAATTCGATTTA
GTCCGGTGGCATTCTCACGCCACAAACCAAATCATAAATAACCGCCTCTTTTCCGCCAG

-continued

ATAACTGCAAAATTATAGAACACTGACAGGCTGGAATATCGTCATTTTTCCTAGACGTA
ATATTTCCAAAACAAGCAATCATCGAACTTAATCATTGTAAACCGCTATTTGTATCATA
GCAGGATCGGGAAATATTTTAAGGGGGACGGG

SEQ ID NO: 40
P1100
TTCATTTTCTTGGTCTTTATGCGACCCGCTATAAAATCCCATATCAACAGCCCC
ATTGCCTTTAGGCTGTCTGTTTTGCCTTATTTCCCGTGATAAAAGGGCTATAGTCTGCCT
TTAGTGATTTTTGGGAATGGCAGAATAACGATCC

SEQ ID NO: 41
P1392
GCTTTCTGCGCTCCTCACCATTTTATGGCCGCAATCACCATTCAAAAGTAACCA
TCCACGGAGACGCCGAATCTTTATGACCGTGCGTCGTTATTTTCGGGCTATAGCTTTGC
GGAGTAAATAGGTC

SEQ ID NO: 42
P0326
AAGGCAATTCATCCTGACAGCAGTCTTTAAGCGAAATTTAACATTAAAAAATA
CCTGACCATATTCAACAATGTTTAATTTCACTCCTTGAAAGAAAAAAATAGCGACAATT
TTCTAAAAAACTATCGGCAATACTGGACATCCTATTTTAATCTGGTGTTTTTATATCATA
CAAAACAGGGTAATATAAATAG

SEQ ID NO: 43
P0570
AAGAAATACTCCGATTAAACAGGGGAAATATCAAAAAATATCTTTTAGCTGAT
AGATGATATCAAGCAAATGATGAACTGTTTAAATTTTTAAAACACGAAATAGAAAAAG
GATGGATTGGGCGCC

SEQ ID NO: 44
P1231
ACTTTATTATATTGCTCATCTTTGTTAAAAATTATGTATCGATAAAAGATAAAT
ATCATTTATCTTTTATCGATATTTTTTGATTTTGTCTTTGCGTCCAGAAAAGACAGCATT
CCTTCTCAATAAAGAAATATTATTTTTTGTTTTGAAAAATTTTTCCAAAATCTAGAATG
CTACATTAAATATACAAAAATATTATTATACAAATAAGGCTTTTAAATACCCATATTTTT
TAGAATTTCTTTACAAAGAAACATGTTAAATATAGATTTAGAGATTAATATCAGCCATT
TTTATCAAAAATTCTTTTTTTGTTTTATAATATTATGCTGCAAAACTAATAAAAACGCCC
TTTCGAAATTAACGATCACCCACAAGAAATAATTATCTGACAGCGCTTACCAATCAATT
ATTGCCGAACGCAGAGTCCCGTATTAGGACGGTCAACAATCTAAACCGTTTTTCAGAAA
ATATTGCTTTATAAGCCTCAAAACTTAAAAGCTGCGGTATTTTAATATACCAAAATTTTC
TGGAAAAGCCGGCGAATCAGATAACAGTTCCGCACAGGTGAGAACCACGACGGATCTT
CTCTGAATTGTTGGTTAGTTAAGAAAGAAACAAGGATT

SEQ ID NO: 45
P1980
TGTGTTCTCCTGCTACGAGAACACTTTAATTCTAAAATATATTTTTGATTAGAT
ATATAATTAAAAAGATAGTTATGAATATGATTCATGAATATTTTTTGAGATTAAAAATC
CTCTATTTGAAATAGTATTATTAGGCTTTGTTATTAACGGATATTGTTATTTATAGAGAT
TAAGCAGGCCATTTCAAAAATATCGAGATGATGCGCTCTCTATCAATTTTTGCTTTCTCT
CTCTGTTCCACGTGAAACAAAAGGCCGCATTCCGACAAATTACAGGCTCTTTTCAGGC
TTAAAACAAGGTTGATGATTGTTTTTCATCCCGAAAACTGTTTGATAGCTTTTTTCTGTT
TCTCCCGTCTGG

SEQ ID NO: 46
P1484
TTCGTCTATTCCAAAGAGATTTATTCAAATATCACTATAAAATAGGTCGCTTCG
GGATAGAAAACAGTCGGTCTTCCCTATTTTAATTTGATCAAGGTATTCCA

SEQ ID NO: 47
P0145
CGGGTTTAGGACTCCTGCAAAAAAAGGCTTTGTTTCGGATCGGATAAAAGGAT
TAAACGGATTCATCCATCGTTATGTTTAATTTTAGATTTTTTATCCCTGAATAGCGAGGG
GTATACATCACTGTTTTTTGGGAAAAAACGGCGGTGAAATTCCTATTTTTCTGTAGCGCT
TTGTGAAGCTTTTCTGGGATATTTGGCTTTTTGCCTTGTTCTTTATCGTATTTTTTGGGTT
TTTACCGGAAAATGCTCTGATGCTATATCGGTTTTGTGCTTTTTCCCGACTTTTCGGGCT
TTGTTCCGAAATATCGGGAAAATCGGTTGGAAATCAGGAAAAAA

SEQ ID NO: 48
P0101
AGGGGGAACCTTTCAGTGACCAAGGCACAAAATAGTGCCGGATTGCGGATAA
TTTCCAGAACAGACATGCTCCTGACAGAAGCTTGTTGAAAAGGAAATATCAATT

SEQ ID NO: 49
P1194
AAAATATCCATCAAGGCTCGACGTAATCTGCTTCAAATCAGAAATTTAACAAG
GCCTATATTTTTATTAGACCGTCTATGTCTTTAATTTTTGAAAATACTACCGCCAGAC
CACAAAATATGTCTCACATGGGTTGTTTTAAAAATTTTCATTACCCAAAAATTGAAATT

-continued

TGCTTTCTTTTAATGTGATAACAGGGGTTTTAGCCTGAAATCATTTGACCTTGCTTTCCC
TATTTCATTCCGCTTTAAAGCTTCCATTTTGAAGCATATTTGAATGATAAAGGCAGGATT
C

SEQ ID NO: 50
1644
TATCTTCCTTCAGAATTTGAGACGCTGCCTTGTCAGATGGTCTGCAATGCCGTC
TCCTAAAAGTAAAGACAGCCTTGCGATAATATAACTGCCAGATAAATCCGGCTATCAA
GATAAAAGCCAAGCTCGACCTTAATTTACGGAGATTACCGGAAAAAATCGAAACGAAA
GAGTTGAACTCTGCTTTTGACCGATTATGCCATGAGCT

SEQ ID NO: 51
P1582
AAACGGTTACTGGGCTTTAGCTGCCTTGTAAAAGGTATCTTCATAGCCTTAAAA
ACAGAAAAACCGGCCTGATTTTTCAGGTCGGTTTTTTATTACTTTAACTTCGATTATATC
GCAGATTTTAGAAAGAATGACGCGCTTGAGTTTCGCAAATTCAAAGCTACCCTGACATT
ATCTAACTCTCAATTCTTATCTCACAGCGATAATTTCGCCCCAGAAAACTGCTCTAAGC
ACACTGCCTACGAAAAATCCAAAATCACTATAAAGGCCAAGCCTGCGGCTTTCCTATAA
AAACCATTCTTACCTTTAGGATCTGGCTGTCCCGTTCTATCATTAGACTTTCATTCTACG
TCAAAAAAGGGGAGGGGGTA

SEQ ID NO: 52
P0005
GTAAATTGGCCTAACCGCCTTTTAAAAAATCACCTGAAAAGGACAGCCGGCTT
TAAATATTTTAAATGCCGGCCAAAGGCGTTTTACCTAAACTTTAGGGCAGTAAAGAAAA
GCTAACTGTCCTTTCAAAGATAGGGGCTGCTAAGTCCTATTCAAAATCAAAGGCTTGCC
TCTCTATTTACTTTCAGGCTTCGTTGAATGAACAGAGATAGAGCTGCAATCTGCGACAA
AACTGGATAATAGGTTAGGGGCTCTGTTCCAAAGGTTGTT

SEQ FD NO: 53
P0300
GGCATGTTCGCGGCCGCCGGTTCCGATAAGCAGGACGTTC

What is claimed is:

1. A method for identifying biological parts based on a dual-fluorescent reporter gene system, comprising steps of:
   - (S1) with pEZ15Asp plasmids as a skeleton, constructing a single-fluorescent reporter gene system, and screening fluorescent proteins;
   - (S2) according to expressions of different fluorescent protein genes in Zymomonas mobilis (Z. mobilis hereinafter), screening suitable fluorescent reporter genes, respectively named as a first fluorescent reporter gene and a second fluorescent reporter gene;
   - (S3) with pEZ15Asp as a template, respectively designing a forward primer and a reverse primer, conducting PCR (Polymerase Chain Reaction) amplification, and obtaining a pEZ15Asp skeleton;
   - (S4) with utilizing a modified Gibson assembly method, connecting first promoter-first fluorescent reporter gene and second promoter-second fluorescent reporter gene to the pEZ15Asp skeleton, adding a terminator between the two fluorescent reporter genes, and obtaining the dual-fluorescent reporter gene system;
   - (S5) with the dual-fluorescent reporter gene system as a template, respectively designing a forward primer and a reverse primer, conducting PCR amplification, and obtaining a dual-fluorescent reporter gene system skeleton;
   - (S6) through the modified Gibson assembly method, transforming the biological parts to be detected and the dual-fluorescent reporter gene system skeleton obtained in the step of S5 into Escherichia coli DH5α; verifying positive clones on a plate by PCR; after culturing overnight, extracting plasmids; and
   - (S7) transforming the plasmids extracted in the step of S6 into ZM4 competent cells; activating and culturing to a logarithmic phase, then detecting and verifying with a flow cytometer.

2. The method, as recited in claim 1, wherein: in the step of S1, the fluorescent proteins are all promoted by a promoter PlacUV5; the fluorescent proteins are one of EGFP, mCherry, RFP, CFP, and opEGFP, opmCherry and opCFP after being optimized by a codon.

3. The method, as recited in claim 2, wherein: in the step of S2, the first promoter is Ptet; the second promoter is PlacUV5; the first fluorescent reporter gene and the second fluorescent reporter gene are respectively EGFP and opmCherry.

4. The method, as recited in claim 1, wherein: in the step of S3, the forward primer and the reverse primer are respectively a first primer and a second primer; sequences of the first primer and the second primer respectively refer to SEQ ID NO: 1 and SEQ ID NO: 2.

5. The method, as recited in claim 1, wherein: in the step of S5, the forward primer and the reverse primer are respectively a primer Prtt-F and a primer Prtt-R; sequences of the primer Prtt-F and the primer Prtt-R respectively refer to SEQ ID NO: 3 and SEQ ID NO: 4; or
   in the step of S5, the forward primer and the reverse primer are respectively the primer Prtt-F and a primer PgapTSS-R; sequences of the primer Prtt-F and the primer PgapTSS-R respectively refer to SEQ ID NO: 3 and SEQ ID NO: 4.

6. The method, as recited in claim 1, wherein: in the step of S6, the biological parts to be detected are endogenous promoters of different intensities, promoters containing synthetic RBS (Ribosome Binding Site) sequences of different intensities, terminators of different intensities, or sRNA-UTR (soluble Ribonucleic Acid-Untranslated Region) interaction pairs.

7. The method, as recited in claim 6, wherein: the biological parts to be detected are the endogenous promoters of different intensities or the promoters containing the synthetic RBS sequences of different intensities; the promoters containing the RBS sequences of different intensities are obtained through steps of:
   - (Sa) predicting the RBS sequences of different intensities; and
   - (Sb) with the dual-fluorescent reporter gene system as a template, conducting PCR amplification with a primer pEZ-tetR-F and a primer RBS-R, wherein lowercases at a 5' terminal of each primer are homologous arms of the dual-fluorescent reporter gene system; and obtaining the promoters containing the RBS sequences of specific intensities.

8. The method, as recited in claim 6, wherein: the biological parts to be detected are the terminators of different intensities; the terminators of different intensities are obtained through steps of:
   - (S01) screening a gene set whose contiguous genes in a same transcription direction have large expression differences, and ordering according to the expression differences;
   - (S02) with a bioinformatics method, predicting terminator sequences between the contiguous genes, and representing the intensities of the terminators by the expression differences between the contiguous genes; and
   - (S03) designing primers for a target terminator sequence, conducting PCR amplification, and obtaining terminator fragments.

9. The method, as recited in claim 6, wherein: the biological parts to be detected are the sRNA-UTR interaction pairs; UTR fragments are obtained through steps of:
   - (S0a) with a bioinformatics method, analyzing a target sequence; after determining a transcriptional start site, retaining the sequence from the transcriptional start site to 99-bp after an initiation codon ATG; as a target 5' UTR sequence;

(S0b) with a Z. mobilis genome as a template, designing a forward primer and a reverse primer, conducting PCR amplification, and obtaining the target UTR sequence fragments;

with a dual-fluorescent reporter gene system containing a promoter Pgap as a template, conducting PCR amplification, and obtaining the dual-fluorescent reporter gene system skeleton.

10. The method, as recited in claim 7, wherein: in the step of S7, the plasmids are electronically transformed into the ZM4 competent cells, particularly comprising steps of:
   (1) placing the ZM4 competent cells on ice; after the ZM4 competent cells melt, taking 50 μL of the competent cells and adding into an electro-transformation cup, and then adding 1 μg of the plasmids into the electro-transformation cup, wherein electro-transformation conditions are 1600 V, 25 μF and 200 Ω;
   (2) after completing electro-transformation, resuscitating at 30° C. in RM (Rich Media);
   (3) centrifuging a culture, which is obtained after 6-12 hours of resuscitation, with a rotational speed of 6000 rpm for 1 minute, so as to remove a supernatant;
   (4) adding 200 μL of fresh RM; taking a sample of 100 μL and coating on a resistant plate containing corresponding antibiotics; and culturing at 30° C. for 2 days; and
   (5) conducting PCR positive clone verification with a primer Pdual-F and a primer Pdual-R, wherein:

```
a sequence of the Pdual-F is
CCGCTCACAATTCCACACATTATAC, referring to
SEQ ID NO: 8;
and a sequence of the Pdual-R is
ACCAGGATGGGCACCAC, referring to
SEQ ID NO: 9.
```

11. The method, as recited in claim 10, wherein: in the step of S7, the intensities are detected and verified with the flow cytometer, particularly comprising steps of:
   (1) activating and culturing mono-clones, which are loaded into the dual-fluorescent reporter gene system and verified to be correct by PCR positive clone verification, in RM containing corresponding antibiotics;
   (2) after culturing to the logarithmic phase, taking a sample of 200 μL; centrifuging with a rotational speed of 12000 rpm for 1 minute, so as to remove a supernatant; washing with 1×PBS (Phosphate Buffered Saline) for two times, and re-suspending;
   (3) detecting with the flow cytometer, wherein a cell collection event is set to be 20,000.

12. A method for characterizing a biological part based on a dual-fluorescent reporter gene system, wherein the biological part is an endogenous promoter Pgap with a SEQ ID of NO: 5, comprising steps of:
   (S1) with a pEZ15Asp plasmids as a skeleton, constructing different single-fluorescent reporter gene systems, and screening different fluorescent proteins;
   (S2) according to expression values of different fluorescent protein genes in Zymomonas mobilis (Z. mobilis hereinafter), screening EGFP (Enhanced Green Fluorescent Protein) and opmCherry, respectively named as a first fluorescent reporter gene and a second fluorescent reporter gene; choosing Ptet and PlacUV5 for the first and second fluorescent reporter genes, respectively named as a first promoter and a second promoter;
   (S3) with pEZ15Asp as a template, respectively designing a forward primer and a reverse primer, conducting PCR (Polymerase Chain Reaction) amplification, and obtaining a pEZ15Asp skeleton;
   (S4) utilizing a modified Gibson assembly method, connecting first promoter-first fluorescent reporter gene and second promoter-second fluorescent reporter gene to the pEZ15Asp skeleton, adding a terminator between the two fluorescent reporter genes, and obtaining the dual-fluorescent reporter gene system; wherein: the first promoter-first fluorescent reporter gene is Ptet-EGFP, and the second promoter-second fluorescent reporter gene is PlacUV5-opmCherry;
   (S5) with the dual-fluorescent reporter gene system as a template, respectively designing a forward primer and a reverse primer, conducting PCR amplification, and obtaining a dual-fluorescent reporter gene system skeleton;
   (S6) through the modified Gibson assembly method, separately transforming the endogenous promoter Pgap, and the dual-fluorescent reporter gene system skeleton obtained in the step of S5, into Escherichia coli DH5α; verifying positive clones on a plate by PCR; after culturing overnight, extracting plasmids; and
   (S7) transforming the plasmids extracted in the step of S6 into Zymomonas mobilis ZM4 (ZM4 hereinafter) competent cells; activating and culturing to a logarithmic phase.

13. The method, as recited in claim 12, wherein: in the step of S1, expressions of the different fluorescent proteins are all driven by a promoter PlacUV5; the fluorescent proteins are one of EGFP, mCherry, RFP (Red Fluorescent Protein), CFP (Cyan Fluorescent Protein), opEGFP, opmCherry, and opCFP.

14. The method, as recited in claim 12, wherein: in the step of S3, the forward primer and the reverse primer are respectively a first primer and a second primer; sequences of the first primer and the second primer respectively refer to SEQ ID NO: 1 and SEQ ID NO: 2.

15. The method, as recited in claim 12, wherein: in the step of S5, the forward primer and the reverse primer are respectively a primer Prtt-F and a primer Prtt-R; sequences of the primer Prtt-F and the primer Prtt-R respectively refer to SEQ ID NO: 3 and SEQ ID NO: 4; or
   in the step of S5, the forward primer and the reverse primer are respectively the primer Prtt-F and a primer PgapTSS-R; sequences of the primer Prtt-F and the primer PgapTSS-R respectively refer to SEQ ID NO: 3 and SEQ ID NO: 65.

16. The method, as recited in claim 12, wherein: the endogenous promoter Pgap is obtained through steps of: with ZM4 as a template, conducting PCR amplification with a primer P0177-F and a primer P0177-R, and obtaining the endogenous promoter Pgap, wherein: sequences of the primer P0177-F and the primer P0177-R respectively refer to SEQ ID NO: 6 and SEQ ID NO: 7; recovering and purifying a PCR product of the endogenous promoter Pgap using a PCR recovery kit.

17. The method, as recited in claim 16, wherein: in the step of S7, the plasmids are electronically transformed into the ZM4 competent cells, particularly comprising steps of:
   (1) placing the ZM4 competent cells on ice; after the ZM4 competent cells melt, taking 50 μL of the competent cells and adding into an electroporation cuvette, and then adding 1 μg of the plasmids into the electroporation cuvette, wherein electroporation conditions are 1600 V, 25 μF and 200 Ω;

(2) after completing electroporation, resuscitating at 30° C. in RM (Rich Medium);

(3) centrifuging a culture, which is obtained after 6-12 hours of resuscitation, with a rotational speed of 6,000 rpm for 1 minute, so as to remove a supernatant;

(4) adding 200 μL fresh RM; taking a sample of 100 μL and plating on a resistant plate containing corresponding antibiotics; and culturing at 30° C. for 2 days; and (5) conducting colony PCR and selecting positive clones with a primer Pdual-F and a primer Pdual-R, wherein: sequences of the primer Pdual-F and primer Pdual-R respectively refer to SEQ ID NO: 8 and SEQ ID NO: 9.

18. A biological part library constructed by the method for characterizing the biological part based on the dual-fluorescent reporter gene system as recited in claim 12.

* * * * *